(12) United States Patent
Goetinck et al.

(10) Patent No.: US 6,566,489 B1
(45) Date of Patent: May 20, 2003

(54) SYNDECAN-4 BINDING PROTEIN (S4BP) AND USES THEREOF

(75) Inventors: Paul F. Goetinck, Boston, MA (US); Peter C. Baciu, Laguna Niguel, CA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/526,400

(22) Filed: Mar. 15, 2000

Related U.S. Application Data

(60) Provisional application No. 60/124,497, filed on Mar. 15, 1999.

(51) Int. Cl.[7] .............................................. C07K 14/00
(52) U.S. Cl. ........................ 530/300; 530/326; 530/350
(58) Field of Search ................................. 530/350, 300, 530/326

(56) References Cited

PUBLICATIONS

Schmelz et al. 1993; Eur. J. Cell. Biol. 61: 274–289.*
Geisse et al., Eukaryotic Expression Systems: A Comparison; Protein Expression and Purification. (1996), vol. 8, pp. 271–282.
Pharmacia Biotech Catalog (1996) pp. 107 and 110–117.
Baciu et al., "Molecular Cloning and Genomic Organization of Chicken Syndecan–4," Journal of Biological Chemistry, Jan. 7, 1994, vol. 269, No. 1, pp. 696–703.
Baciu et al., "Protein Kinase C Regulates the Recruitment of Syndecan–4 into Focal Contacts", Molecular Biology of the Cell, Nov. 1995, vol. 6, No. 11, pp. 1503–1513.
Burridge et al., "Focal Adhesions, Contractility, and Signaling," Annual Review of Cell and Developmental Biology, 1996, vol. 12, pp. 463–518.
Carey, "Syndecans: multifunctional cell–surface co–receptors," Biochem. J., 1997, vol. 327, pp. 1–16.
Liu et al., "Heparan Sulfate Proteoglycans as Adhesive and Anti–invasive Molecules," The Journal of Biological Chemistry, Aug. 28, 1998, vol. 273, No. 35, pp. 22825–22832.
Martinho et al., "Ligand Binding to Heparan Sulfate Proteoglycans Induces Their Aggregation and Distribution along Actin Cytoskeleton," Molecular Biology of the Cell, Nov. 1996, vol. 7, No. 11, pp. 1771–1788.
Oh et al., "Syndecan–4 Proteoglycan Regulates the Distribution and Activity of Protein Kinase C," The Journal of Biological Chemistry, Mar. 28, 1997, vol. 272, No. 13, pp. 8133–8136.
Oh et al., "Multimerization of the Cytoplasmic Domain of Syndecan–4 Is Required for Its Ability to Activate Protein Kinase C," Journal of Biological Chemistry, May 2, 1997, vol. 272, No. 18, pp. 11805–11811.
Oh et al., "Syndecan–4 Proteoglycan Cytoplasmic Domain and phosphatidylinositol 4,5–Bisphosphate Coordinately Regulate Protein Kinase C Activity," Journal of Biological Chemistry, Apr. 24, 1998, vol. 273, No. 17, pp. 10624–10629.
Resh, "Myristylation and Palmitylation of Src Family Members: The Fats of the Matter," Cell, Feb. 11, 1994, vol. 76, No. 3, pp. 411–413.
Towler et al., "Amino–terminal Processing of Proteins by N–Myristoylation," Journal of Biologi al Chemistry, Jan. 25, 1987, vol. 262, No. 3, pp. 1030–1036.
Vainio et al., "Expression of Syndecan Gene Is Induced Early, Is Transient, and Correlcs with Changes in Mesenchymal Cell Proliferation during Tooth Organogenesis," Developmental Biology, Oct. 1991, vol. 147, No. 2, pp. 322–333.
Woods et al., "Protein kinase C involvement in focal adhesion formation," Journal of Cell Science, Feb. 1992, vol. 101, Part 2, pp. 277–290.
Woods et al., "Syndecan 4 Heparan Sulfate Proteoglycan Is a Selectively Enriched and Widespread Focal Adhesion Component," Molecular Biology of the Cell, Feb. 1994, vol. 5, No. 2, pp. 183–192.
Woods et al., "Syndecans: synergistic activators of cell adhesion," Trends in Cell Biology, May 1998, vol. 8, No. 5, pp. 189–192.

* cited by examiner

Primary Examiner—Karen Cochrane Carlson
(74) Attorney, Agent, or Firm—Fish & Richardson PC

(57) ABSTRACT

The present invention relates to a gene encoding a novel protein, syndecan-4 binding protein (S4BP), which binds to syndecan-4. S4BP polypeptides play a role in cell matrix interactions. Described herein are isolated and antisense nucleic acids molecules, recombinant expression vectors, host cells and non-human transgenic animals containing an insertion or a disruption of the S4BP gene. Diagnostic, screening and therapeutic methods utilizing the compositions of the invention are also provided.

25 Claims, 2 Drawing Sheets

Amino Acid and Nucleotide Sequence of Syndesmos

```
ggcacgagcg cccgcccgcc ggcggcgagg cg atg gcg gcc atg gga gcc atg    53
                                     Met Ala Ala Met Gly Ala Met
                                      1               5 gga gtg atg gcg gcc gta gga gcg ttg ccg gcg ggc gcg ggg tcc ctc   101
Gly Val Met Ala Ala Val Gly Ala Leu Pro Ala Gly Ala Gly Ser Leu
         10              15              20 ccg ccg ctg ccg acg ctg ggg gtg ccc ggc gtg ccc gag ctg aag ccg   149
Pro Pro Leu Pro Thr Leu Gly Val Pro Gly Val Pro Glu Leu Lys Pro
     25              30              35 ctg acg cgg tac gag gcc atg cgg ctg ggc ccg ggc tgg agc cac tcg   197
Leu Thr Arg Tyr Glu Ala Met Arg Leu Gly Pro Gly Trp Ser His Ser
 40              45              50              55 tgc cac gcc atg ctg tac gcg ccc aac ccg ggc atg ctg ttc ggc cgc   245
Cys His Ala Met Leu Tyr Ala Pro Asn Pro Gly Met Leu Phe Gly Arg
                 60              65              70 atc ccg ctg cgc tac gcc gtg ctg atg cag atg cgc ttt gac ggc cta   293
Ile Pro Leu Arg Tyr Ala Val Leu Met Gln Met Arg Phe Asp Gly Leu
             75              80              85 ctg ggc ttc ccc ggg ggg ttc gtg gac cgc cgg tac tgg tcc ctg gag   341
Leu Gly Phe Pro Gly Gly Phe Val Asp Arg Arg Tyr Trp Ser Leu Glu gac ggt ctg aac cgg gtg ctg ggc ctg ggc ctg ggc tgc gtg cgc ctg   389
Asp Gly Leu Asn Arg Val Leu Gly Leu Gly Leu Gly Cys Val Arg Leu
     105             110             115 acg gag gcc gac tac ctg tgc tcg cac ctg acg gac ggg ccg cat cgc   437
Thr Glu Ala Asp Tyr Leu Cys Ser His Leu Thr Asp Gly Pro His Arg
120             125             130             135 gtg gtg gct cac tta tac gcc cgg cag ctg acc ctg gag gag ctg cac   485
Val Val Ala His Leu Tyr Ala Arg Gln Leu Thr Leu Glu Glu Leu His
                 140             145             150 acc atc gag atc agc gcg gtg cac tcc cga gac cac ggg ctg gag gtg   533
Thr Ile Glu Ile Ser Ala Val His Ser Arg Asp His Gly Leu Glu Val
             155             160             165
```

FIG. 1A

```
atg ggc atg gtc cgt gtc ccc ctc tac acc cag aaa gat cgc atg ggt    581
Met Gly Met Val Arg Val Pro Leu Tyr Thr Gln Lys Asp Arg Met Gly
        170                 175                 180 ggg ctg cca aac ttc ctg gcc aac tcc ttc gtt gga act gcc aaa ttc    629
Gly Leu Pro Asn Phe Leu Ala Asn Ser Phe Val Gly Thr Ala Lys Phe
        185                 190                 195 cag ctg ctc ttt gct ctg aag atc ttg aac atg gtg ccg gag gag aag    677
Gln Leu Leu Phe Ala Leu Lys Ile Leu Asn Met Val Pro Glu Glu Lys
200                 205                 210                 215 ctg gcc gag gcg gtg gct gcc acg cag aag ccg aag aag ccg gcg atc    725
Leu Ala Glu Ala Val Ala Ala Thr Gln Lys Pro Lys Lys Pro Ala Ile
                220                 225                 230 gac cac gcg gct gtg gca gca gca aag cag gcg aac gag ctg gcg gcg    773
Asp His Ala Ala Val Ala Ala Ala Lys Gln Ala Asn Glu Leu Ala Ala
                235                 240                 245 gcc gcc aga gca ggc aat gaa tac gca gat agc gga gag aac cag gca    821
Ala Ala Arg Ala Gly Asn Glu Tyr Ala Asp Ser Gly Glu Asn Gln Ala
            250                 255                 260 gct gcg cac gct gcg gcc gag ctg gca gag cag cag gcg gcc ggg ctg    869
Ala Ala His Ala Ala Ala Glu Leu Ala Glu Gln Gln Ala Ala Gly Leu
            265                 270                 275 gag agc cag gct gtg ctg gag cat ctg gcg gcc gtg ccg ggg gct gag    917
Glu Ser Gln Ala Val Leu Glu His Leu Ala Ala Val Pro Gly Ala Glu
280                 285                 290                 295 gcc gtg gtg gcg gag ctg cac gcg cag ccc ggg gca gac gct gtg ctg    965
Ala Val Val Ala Glu Leu His Ala Gln Pro Gly Ala Asp Ala Val Leu
                300                 305                 310 gag cag ccg gtg gct gag gcc atg gag tgatgccccc gtgtttgtaa         1012
Glu Gln Pro Val Ala Glu Ala Met Glu
                315             320
ttgattaaaa gtgggtgagg agactagaga ctttcttcta acttcccaac cagttgctgg 1072
ctgcgagatt ccgctgtgta gccaggaggg tttggaattg tctgaagcag gggaaagcta 1132
tgtatttta tggccattaa actctagcga gcttcccaga tcaaaaaaaa            1182
```

FIG. 1B

SYNDECAN-4 BINDING PROTEIN (S4BP) AND USES THEREOF

This application claims the benefit of a previously filed Provisional Application No. 60/124,497, filed Mar. 15, 1999, the contents of which is incorporated in its entirety.

BACKGROUND OF THE INVENTION

Cell morphology, migration, growth and differentiation result from both adhesion dependent and growth factor receptor mediated signaling events. Adhesion dependent signaling events link the extracellular matrix with the intracellular cytoskeleton both structurally and biochemically through the formation of macromolecular complexes at sites of cell matrix interactions. In cell culture, these macromolecular complexes are referred to as focal adhesions. Burridge and Chrzanowska-Wodnicka (1996) *Ann. Rev. Cell. Dev. Biol.* 12:463–518. The ability of adhesion receptors to mediate both signaling and structural events occurs, in part, through the association of their cytoplasmic domains with cytoskeletal components. The cytoskeletal components in turn provide structural and adapter functions for the assembly of the intracellular signaling complexes. Cytoskeletal proteins that provide structural and/or adapter functions include actin, alpha-actinin, paxillin, talin, tensin and vinculin. Associated signaling proteins include tyrosine kinases (focal adhesion kinase, src, csk and fyn), the serine-threonine kinase families of PKC and MAPK and members of the RAS family of small GTP binding proteins. Clark and Brugge (1996) *Science* 268:233–239; Burridge and Chrzanowska-Wodnicka (1996) *Ann. Rev. Cell. Dev. Biol.* 12:463–518.

Members of the syndecan family of cell surface heparan sulfate proteoglycans (syndecan-1 through 4) have been implicated in mediating cell adhesion and morphology. Bernfield et al. (1991) *Ann. Rev. Cell Biol.* 8:365–393; Carey (1997) *Biochem. J.* 327:1–16; Liu et al. (1998) *J. Biol. Chem.* 273:22825–22832; Woods and Couchman (1998) *Trends Cell Biol.* 8:189–192. All four syndecan family members contain a high degree of sequence conservation of their cytoplasmic domains, which, based on homology can be divided into conserved membrane proximal, variable central, and conserved C-terminal subdomains. Several cellular components which associate, either directly or indirectly, with the cytoplasmic domain of syndecan family members have been identified. These include: PKCα and phosphatidyl inositol 4,5-biphosphate (PIP2) which interact directly with the variable central region of the cytoplasmic domain of syndecan-4 (Oh et al. (1997) *J. Biol. Chem.* 272:11805–11811; Oh et al. (1997) *J. Biol. Chem.* 272:8133–8136; Oh et al. (1998) *J. Biol. Chem.* 273:10624–10629); the PDZ containing proteins syntenin (Grootjans et al. (1997) *Prot. Natl. Acad. Sci. USA* 94:13683–13688) and CASK/LIN-2 (Cohen et al. (1998) *J. Cell Bio.* 142:129–138; Hsueh et al. (1998) *J. Biol. Chem.* 142:139–151) which interact with the cytoplasmic domains of all syndecan family members through the highly conserved C-terminal EFYA sequence, and a Src-cortactin complex which associates with the membrane proximal domain of syndecan-3. Kinnunen et al. (1998) *J. Biol. Chem.* 273:10702–10708.

Syndecan-4 is observed in focal contacts (Woods and Couchmana (1994) *Mol. Biol. Cell* 5:183–192; Baciu and Goetinck (1995) *Mol. Biol. Cell* 1:1503–1513) and associates with PKCα (Oh et al. (1997) *J. Biol. Chem.* 272:11805–11811; Oh et al. (1997) *J. Biol. Chem.* 272:8133–8136).

SUMMARY OF THE INVENTION

The present invention is based, in part, on the discovery of a gene which encodes a novel cellular protein referred to herein as syndecan-4 binding protein (S4BP). The S4BP protein was found to interact with the cytoplasmic domain of syndecan-4 but not other members of the syndecan family. When S4BP is overexpressed, it mediates cell spreading and actin cytoskeleton organization. S4BP plays a role in linking syndecan-4 to the focal adhesion complex.

Accordingly, in one aspect, the invention features an isolated nucleic acid molecule (e.g., cDNAs) comprising a nucleotide sequence encoding an S4BP protein or a biologically active portion thereof, as well as, nucleic acid fragments suitable as primers or hybridization probes for the detection of S4BP-encoding nucleic acid (e.g., mRNA). In particularly preferred embodiments, the isolated nucleic acid molecule includes the nucleotide sequence of SEQ ID NO: 1, or the coding region (SEQ ID NO:3), or a complement of these nucleotide sequences. In other particularly preferred embodiments, the isolated nucleic acid molecule of the invention includes a nucleotide sequence which hybridizes, preferably under stringent conditions, to or has at least about 60–65%, preferably at least about 70–75%, more preferably at least about 80–85%, and even more preferably at least about 90–95%, 96%, 97%, 98% or 99% sequence identity to the nucleotide sequence shown in SEQ ID NO:1, or a portion thereof. In other preferred embodiments, the isolated nucleic acid molecule encodes the amino acid sequence of SEQ ID NO:2. The preferred S4BP nucleic acid encodes a protein which also preferably possesses at least one of the S4BP activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2, e.g., sufficiently homologous to an amino acid sequence of SEQ ID NO:2 such that the protein or portion thereof maintains an S4BP biological activity. Preferably, the protein or portion thereof encoded by the nucleic acid molecule maintains the ability to play a role in cell matrix interactions. In one embodiment, the protein encoded by the nucleic acid molecule has at least about 60–70%, preferably at least about 80–85%, and more preferably at least about 86, 88, 90%, and most preferably at least about 90–95%, 96%, 97%, 98% or 99% sequence identity to the amino acid sequence of SEQ ID NO:2 (e.g., the entire amino acid sequence of SEQ ID NO:2). In another preferred embodiment, the protein is a full length protein which is substantially homologous to the entire amino acid sequence of SEQ ID NO:2 (encoded by the open reading frame shown in SEQ ID NO:3). In another embodiment, the protein is a mammalian protein, e.g., a human protein, which is substantially homologous to the amino acid sequence of SEQ ID NO:2, or a portion thereof.

In yet another embodiment, the isolated nucleic acid molecule encodes a portion of an S4BP protein which includes a sequence encoding a SH3 domain binding site motif. Preferably, the SH3 domain binding site motif encoded by the nucleic acid molecule has at least about 80% or more sequence identity to the SH3 domain binding site motif (i.e., about amino acid residues 24 to 27) of SEQ ID NO:2. Preferably, the SH3 domain binding site motif has a consensus sequence Pro-Xaa-Pro-Pro, where Xaa is any amino acid.

In another preferred embodiment, the isolated nucleic acid molecule encodes an S4BP protein or portion thereof which has at least about 55% or more sequence identity to SEQ ID NO:2 and has one or more of the following activities involved with cell matrix interactions: 1) it interacts, directly or indirectly, with syndecan-4; 2) it interacts, directly or indirectly, with paxillin; 3) it interacts, directly or indirectly, with intracellular signaling proteins (e.g., GTP binding protein, focal adhesion kinase, serine-threonine kinase); 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with PKCα; 6) it modulates actin stress fiber formation and/or organization; 7) it plays a role in an adhesion formation signaling pathway; 8) it modulates cell attachment; and/or 9) it modulates cell spreading.

In another embodiment, the isolated nucleic acid molecule is at least 15 nucleotides in length and hybridizes under stringent conditions to a nucleic acid molecule comprising the nucleotide sequence of SEQ ID NO:1 or SEQ ID NO:3. Preferably, the isolated nucleic acid molecule corresponds to a naturally-occurring nucleic acid molecule. More preferably, the isolated nucleic acid encodes naturally-occurring S4BP or a biologically active portion thereof. Preferably, the biologically active portion is preferably encoded by a nucleotide sequence greater than 150, 200, 300, 400, 500, 600, 700 or 1000 base pairs in length. Moreover, given the disclosure herein of S4BP-encoding cDNA sequences (e.g., SEQ ID NO:1), antisense nucleic acid molecules (i.e., molecules which are complementary to the coding strand of the S4BP cDNA sequence) are also provided by the invention.

In a preferred embodiment, the encoded S4BP protein differs in amino acid sequence at least 1 to as many as (but not more than) 2, 3, 5, 10, 20 or 40 residues from a sequence in SEQ ID NO:2. In a preferred embodiment, the differences, however, are such that: the S4BP encoded protein exhibits an S4BP biological activity, e.g., the encoded S4BP protein retains a biological activity of a naturally occurring S4BP, e.g., the S4BP protein of SEQ ID NO:2.

In preferred embodiments, the encoded polypeptide includes all or a fragment of an amino acid sequence from SEQ ID NO:2, fused, e.g., in reading frame, to additional amino acid residues, preferably to residues encoded by genomic DNA 5' to the genomic DNA which encodes a sequence from SEQ ID NO:2.

In preferred embodiments the encoded S4BP protein includes an S4BP sequence described herein as well as other N-terminal and/or C-terminal amino acid sequence.

In another aspect, the invention features vectors, e.g., recombinant expression vectors, containing the nucleic acid molecules of the invention and host cells into which such vectors have been introduced. In one embodiment, such a host cell is used to produce S4BP protein by culturing the host cell in a suitable medium. The S4BP protein can be then isolated from the medium or the host cell.

In yet another aspect, the invention features a transgenic nonhuman animal, e.g., a rodent (e.g., a mouse), or a cow, goat, pig, rabbit or guinea pig, in which an S4BP gene has been introduced or altered. In one embodiment, the genome of the nonhuman animal has been altered by introduction of a nucleic acid molecule of the invention encoding S4BP as a transgene. In another embodiment, an endogenous S4BP gene within the genome of the nonhuman animal has been altered, e.g., functionally disrupted, by homologous recombination.

In still another aspect, the invention features an isolated S4BP protein or a portion, e.g., a biologically active portion, thereof. In a preferred embodiment, the isolated S4BP protein or portion thereof plays a role in cell matrix interaction. In another preferred embodiment, the isolated S4BP protein or portion thereof is sufficiently homologous to an amino acid sequence of SEQ ID NO:2 such that the protein or portion thereof maintains one or more S4BP activity.

In one embodiment, the biologically active portion of the S4BP protein includes a domain or motif, preferably a domain or motif which has an S4BP activity. The motif can be, e.g., a SH3 binding domain site motif, and/or at least one or two myristoylation motif(s).

The invention also provides an isolated preparation of an S4BP protein. In preferred embodiments, the S4BP protein includes the amino acid sequence of SEQ ID NO:2. In another preferred embodiment, the invention pertains to an isolated full length protein which is substantially homologous to the entire amino acid sequence of SEQ ID NO:2 (encoded by the open reading frame shown in SEQ ID NO:3). In yet another embodiment, the protein has at least about 60–70%, preferably at least about 80–85%, and more preferably at least about 86, 88, 90%, and most preferably at least about 90–95% 96%, 97%, 98% or 99% sequence identity to the entire amino acid sequence of SEQ ID NO:2. In other embodiments, the isolated S4BP protein includes an amino acid sequence which has at least about 60–70% or more sequence identity to the amino acid sequence of SEQ ID NO:2 and has an one or more of the following activities: 1) it interacts, directly or indirectly, with syndecan-4; 2) it interacts, directly or indirectly, with paxillin; 3) it interacts, directly or indirectly, with intracellular signaling proteins (e.g., GTP binding protein, focal adhesion kinase, serine-threonine kinase); 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with PKCAα; 6) it modulates actin stress fiber formation and/or organization; 7) it plays a role in an adhesion formation signaling pathway; 8) it modulates cell attachment; 9) it modulates cell spreading.

Alternatively, the isolated S4BP protein can include an amino acid sequence which is encoded by a nucleotide sequence which hybridizes, e.g., hybridizes under stringent conditions, or has at least about 60–65%, preferably at least about 70–75%, more preferably at least about 80–85%, and even more preferably at least about 90–95% 96%, 97%, 98% or 99% sequence identity to the nucleotide sequence of SEQ ID NO:1. It is also preferred that the preferred forms of S4BP also have one or more of the S4BP activities described herein.

In a preferred embodiment, the S4BP protein differs in amino acid sequence at least up to 1 to as many (but not more than) 2, 3, 5, 10, 20, or 40 residues, from a sequence in SEQ ID NO:2. In other preferred embodiments, the S4BP protein differs in amino acid sequence at up to 1, 2, 3, 5, or 10% of the residues from a sequence in SEQ ID NO:2. Preferably, the differences are such that: the S4BP protein exhibits an S4BP biological activity, e.g., the S4BP protein retains a biological activity of a naturally occurring S4BP.

In another aspect, the invention features a fragment of an S4BP protein capable of binding to syndecan-4. In a preferred embodiment, the fragment comprises at least 10, 15, 20, 25, 30, 50, 100, 150 amino acid residues and is capable of binding to syndecan-4.

In another aspect of the invention, the S4BP protein is a recombinant S4BP protein which differs from S4BP isolated from tissue in one or more of the following: its pattern of glycosylation, myristoylation, phosphorylation, or other posttranslational modifications.

Another aspect of the invention features a fragment of a syndecan-4 protein which is capable of binding to syndesmos. In a preferred embodiment, the fragment comprises at least 10, 15, 20, 25, 30 amino acid residues and is capable of binding to syndesmos. Preferably, the syndesmos binding fragment comprises at least 10, 15, 17, 20 or 30 but not more than 20, 28, 30, 40, 50, or 100 amino acid residues of syndecan-4. In a preferred embodiment, the syndesmos binding fragment comprises amino acids 169 to 197 of SEQ ID NO:2 (SEQ ID NO:6) or 180 to 197 of SEQ ID NO:2.

The S4BP protein of the invention, or portions or fragments thereof, can be used to prepare anti-S4BP antibodies. Accordingly, the invention also provides an antigenic peptide of S4BP which includes at least 8 amino acid residues of the amino acid sequence shown in SEQ ID NO:2 and encompasses an epitope of S4BP such that an antibody raised against the peptide forms a specific immune complex with S4BP. Preferably, the antigenic peptide includes at least 10 amino acid residues, more preferably at least 15 amino acid residues, even more preferably at least 20 amino acid residues, and most preferably at least 30, 50, 70, 80 amino acid residues. The invention further provides an antibody, e.g., a monoclonal antibody that specifically binds S4BP. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

In another aspect, the S4BP binding fragment of syndecan-4, can be used to prepare antibodies. Accordingly, the invention also provides an antigenic peptide of syndecan-4 which includes at least 8 to 17 amino acid residues of the amino acid sequence shown in SEQ ID NO:5 and encompasses an epitope of syndecan-4 such that an antibody raised against the peptide forms a specific immune complex with S4BP binding region of syndecan-4. Preferably, the antigenic peptide includes at least 10 amino acid residues, more preferably at least 15 amino acid residues, even more preferably at least 20 amino acid residues, and most preferably at least 30, 50 amino acid residues. The invention further provides an antibody, e.g., a monoclonal antibody that specifically binds S4BP binding region of syndecan-4. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

In another aspect, the invention features, a method of modulating an S4BP mediated property of a cell, in vitro or in vivo. The method includes contacting the cell with an agent which modulates, e.g., inhibits the interaction of S4BP with syndecan-4.

The S4BP/syndecan-4 interaction can be inhibited or reduced by administering an agent which interferes with the binding of S4BP and syndecan-4. Examples of such agents include an antibody, e.g., an intrabody, e.g., an antibody, which binds to S4BP or an antibody which binds to syndecan-4 (e.g., an antibody which binds the S4BP binding region of syndecan-4), or both. Other agents include: an S4BP protein, or a syndecan-4 binding portion thereof; a syndecan-4 protein, or an S4BP binding portion thereof; a fusion of an S4BP protein, or a syndecan-4 binding portion thereof, to another polypeptide, e.g., a polypeptide which promotes entrance into the cell or solubility; a fusion of a syndecan-4 protein, or an S4BP binding portion thereof, to another polypeptide, e.g., a polypeptide which promotes entrance into the cell or solubility; a polypeptide other than S4BP or syndecan-4 which binds to S4BP or syndecan-4, e.g., a polypeptide selected for binding in, e.g., a phage display or 2 hybrid assay. In a preferred embodiment, the method includes administering a nucleic acid which encodes one of the above-described agents.

In a preferred embodiment, the method: modulates cytoskeletal organization, e.g., it modulates the interaction of a matrix receptor (e.g., syndecan-4) and intracellular proteins associated with cytoskeleton (e.g., actin, vinculin); modulates actin stress fiber formation and/or organization; modulates adhesion formation; modulates cell attachment; modulates cell spreading.

In a preferred embodiment, the method includes treating a subject having a disorder characterized by unwanted or aberrant S4BP protein activity or nucleic acid expression.

In a preferred embodiment, the method includes treating a subject having a disorder associated with unwanted or abnormal cellular interactions (e.g., unwanted or abnormal cell-cell and/or cell-matrix interactions, unwanted or abnormal cell migration/movement, e.g., cancer).

In a preferred embodiment, one or more of the following biological activities of S4BP is modulated: 1) it interacts, directly or indirectly, with syndecan-4; 2) it interacts, directly or indirectly, with paxillin; 3) it interacts, directly or indirectly, with intracellular signaling proteins (e.g., GTP binding protein, focal adhesion kinase, serine-threonine kinase); 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with PKCα; 6) it modulates actin stress fiber formation and/or organization; 7) it plays a role in an adhesion formation signaling pathway; 8) it modulates cell attachment; 9) it modulates cell spreading.

In another aspect, the invention features, a method of modulating an S4BP mediated property of a cell, in vitro or in vivo. The method includes contacting the cell with an agent which modulates the activity of S4BP. S4BP activity can be modulated, e.g., transcriptionally, translationally, or post-translationally.

In a preferred embodiment, S4BP activity is modulated by administering: an S4BP antisense molecule; an antibody, e.g., an intrabody, which binds to S4BP; syndecan-4 protein, or an S4BP binding portion thereof; paxillin, or an S4BP binding portion thereof; fusions of a syndecan-4 protein or paxillin, or an S4BP binding portion thereof, to another polypeptide, e.g., a polypeptide which promotes entrance into the cell or solubility; a polypeptide other than syndecan-4 or paxillin which bind to S4BP, e.g., a polypeptide selected for binding in, e.g., a phage display or 2 hybrid assay, a small molecule, e.g., a small molecule which binds to the control region of S4BP. In a preferred embodiment, the method includes administering a nucleic acid which encodes one of the above-described agents.

In a preferred embodiment, the method: modulates cytoskeletal organization, e.g., it modulates the interaction of a matrix receptor (e.g., syndecan-4) and intracellular proteins associated with cytoskeleton (e.g., actin, vinculin); modulates actin stress fiber formation and/or organization; modulates adhesion formation; modulates cell attachment; modulates cell spreading.

In a preferred embodiment, the method includes treating a subject having a disorder characterized by unwanted or aberrant S4BP protein activity or nucleic acid expression.

In a preferred embodiment, the method includes treating a subject having a disorder associated with unwanted or abnormal cellular interactions (e.g., unwanted or abnormal cell-cell and/or cell-matrix interactions, unwanted or abnormal cell migration/movement, e.g., cancer).

In a preferred embodiment, one or more of the following biological activities of S4BP is modulated: 1) it interacts, directly or indirectly, with syndecan-4; 2) it interacts, directly or indirectly, with intracellular signaling proteins (e.g., GTP binding protein, focal adhesion kinase, serine-threonine kinase); 3) it interacts, directly or indirectly, with PKCα; 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with paxillin; 6) it modulates actin stress fiber formation and/or organization; 7) it plays a role in an adhesion formation signaling pathway; 8) it modulates cell attachment; 9) it modulates cell spreading.

In a preferred embodiment, the agent which modulates S4BP activity can be an agent which increases S4BP protein activity or S4BP nucleic acid expression. Examples of agents which increase S4BP protein activity or S4BP nucleic acid expression include small molecules (e.g., small molecules which bind to the promoter region of S4BP), active S4BP proteins, and nucleic acids encoding S4BP that have been introduced into the cell. In another embodiment, the agent which modulates S4BP activity can be an agent which decreases S4BP protein activity or S4BP nucleic acid expression. Examples of agents which inhibit S4BP activity or expression include small molecules, antisense S4BP nucleic acid molecules, and antibodies or intrabodies that specifically bind to S4BP or to its target syndecan-4 or paxillin. In a preferred embodiment, the cell is present within a subject and the agent is administered to the subject.

In another aspect, the invention features, a method of treating a subject having a disorder characterized by unwanted or abnormal cell adhesion or cell spreading (e.g., cancer). The method includes contacting the cell with an agent which modulates, e.g., inhibits, the interaction of S4BP with syndecan-4. In another embodiment, the method includes contacting the cell with an agent which modulates, e.g., inhibits, the interaction of S4BP with paxillin.

The S4BP/syndecan-4 interaction can be inhibited or reduced by administering an agent which interferes with the binding of S4BP and syndecan-4. Examples of such agents include an antibody, e.g., an intrabody, e.g., an antibody, which binds to S4BP or an antibody which binds to syndecan-4 (e.g., an antibody which binds the S4BP binding region of syndecan-4), or both. Other agents include: an S4BP protein, or a syndecan-4 binding portion thereof; syndecan-4 protein, or an S4BP binding portion thereof; a fusion of an S4BP protein, or a syndecan-4 binding portion thereof, to another polypeptide, e.g., a polypeptide which promotes entrance into the cell or solubility; a fusion of a syndecan-4 protein, or an S4BP binding portion thereof, to another polypeptide, e.g., a polypeptide which promotes entrance into the cell or solubility; a polypeptide other than S4BP or syndecan-4 which binds to S4BP or syndecan-4, e.g., a polypeptide selected for binding in, e.g., a phage display or 2 hybrid assay. In a preferred embodiment, the method includes administering a nucleic acid which encodes one of the above-described agents In a preferred embodiment, the method: modulates cytoskeletal organization, e.g., it modulates the interaction of a matrix receptor (e.g., syndecan-4) and intracellular proteins associated with cytoskeleton (e.g., actin, vinculin); modulates actin stress fiber formation and/or organization; modulates adhesion formation; modulates cell attachment; modulates cell spreading.

In another aspect, the invention features, a method of treating a subject having a disorder characterized by unwanted or abnormal cell spreading (e.g., cancer). The method includes contacting the cell with an agent which modulates the activity of S4BP. S4BP activity can be modulated, e.g., transcriptionally, translationally, or post-translationally.

In a preferred embodiment, S4BP activity is modulated by administering: an S4BP antisense molecule; an antibody, e.g., an intrabody, which binds to S4BP; syndecan-4 protein, or an S4BP binding portion thereof; fusions of a syndecan-4 protein, or an S4BP binding portion thereof, to another polypeptide, e.g., a polypeptide which promotes entrance into the cell or solubility; a polypeptide other than syndecan-4 which binds to S4BP, e.g., a polypeptide selected for binding in, e.g., a phage display or 2 hybrid assay, a small molecule, e.g., a small molecule which binds to the control region of S4BP. In a preferred embodiment, the method includes administering a nucleic acid which encodes one of the above-described agents.

In a preferred embodiment the method: modulates cytoskeletal organization, e.g., it modulates the interaction of a matrix receptor (e.g., syndecan-4) and intracellular proteins associated with cytoskeleton (e.g., actin, vinculin); modulates actin stress fiber formation; modulates adhesion formation; modulates cell attachment; modulates cell spreading.

In a preferred embodiment, one or more of the following biological activities of S4BP is modulated: 1) it interacts, directly or indirectly, with syndecan-4; 2) it interacts, directly or indirectly, with paxillin; 3) it interacts, directly or indirectly, with intracellular signaling proteins (e.g., GTP binding protein, focal adhesion kinase, serine kinase); 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with PKCα; 6) it modulates actin stress fiber formation and/or organization; 7) it plays a role in an adhesion formation signaling pathway; 8) it modulates cell attachment; 9) it modulates cell spreading.

The agent which modulates S4BP activity can be an agent which increases S4BP protein activity or S4BP nucleic acid expression. Examples of agents which increase S4BP protein activity or S4BP nucleic acid expression include small molecules e.g., small molecules which bind to the promoter region of S4BP), active S4BP proteins, and nucleic acids encoding S4BP that have been introduced into the cell. In another embodiment, the agent which modulates S4BP activity can be an agent which decreases S4BP protein activity or S4BP nucleic acid expression. Examples of agents which inhibit S4BP activity or expression include small molecules, antisense S4BP nucleic acid molecules, and antibodies or intrabodies that specifically bind to S4BP or to its target syndecan-4. In a preferred embodiment, the cell is present within a subject and the agent is administered to the subject.

In a preferred embodiment, the method includes modulating cell attachment and/or cell spreading.

The invention also features methods for evaluating a subject at risk for a disorder. The method includes evaluating, e.g., detecting, a genetic lesion in the S4BP gene, or evaluating, e.g., detecting, misexpression of the S4BP gene, thereby determining if a subject is at risk for (e.g., has or is predisposed to have) a disorder. The disorder can be one which is characterized by aberrant or abnormal S4BP nucleic acid expression and/or S4BP protein activity, e.g., a disorder associated with abnormal cellular interactions (e.g., abnormal cell-cell and/or cell-matrix interactions, abnormal cell migration/movement). In a preferred embodiment, the method includes evaluating, e.g., in a sample of cells from the subject, the presence or absence of a genetic lesion, e.g., a lesion characterized by an alteration affecting the gene encoding an S4BP protein, or evaluating the misexpression of the S4BP gene. Genetic lesions can be evaluated, e.g., by contacting the sample with a nucleic acid probe capable of hybridizing to S4BP mRNA, e.g., a labeled probe. Expression can be evaluated with an antibody capable of binding to S4BP protein, e.g., a labeled antibody. In a preferred embodiment, the method can also be used in fetal or neonatal diagnosis.

In another aspect, the invention features evaluating, e.g., detecting, a genetic lesion in the syndecan-4 gene, thereby determining if a subject with the lesion is at risk for (e.g., has or is predisposed to have) a disorder characterized by unwanted or abnormal S4BP/syndecan-4 interaction. In one embodiment, the methods include evaluating, e.g., in a sample of cells from the subject, the presence or absence of a genetic lesion characterized by an alteration affecting the gene encoding a syndencan-4 protein or evaluating the misexpression of the syndencan-4 gene. In a preferred embodiment, the methods include evaluating the presence or absence of a genetic lesion affecting the nucleotide sequence encoding the S4BP binding region of syndecan-4. Genetic lesions can be evaluated, e.g., by contacting the sample with a nucleic acid probe capable of hybridizing to syndecan-4 mRNA, e.g., a labeled probe. Expression can be evaluated with an antibody capable of binding to syndecan-4 protein, e.g., an antibody which binds the S4BP binding region of syndecan-4, e.g., a labeled antibody. In a preferred embodiment, the method can also be used in fetal or neonatal diagnosis Another aspect of the invention features methods for detecting the presence of S4BP nucleic acid or protein in a biological sample. In a preferred embodiment, the method involves contacting a biological sample (e.g., a cell sample) with a compound or an agent capable of detecting S4BP protein or S4BP nucleic acid, e.g., mRNA, such that the presence of S4BP nucleic acid or protein is detected in the biological sample. The compound or agent can be, for example, a labeled or labelable nucleic acid probe capable of hybridizing to S4BP mRNA or a labeled or labelable antibody capable of binding to S4BP protein. The invention further provides methods for diagnosis of a subject with, for example, a disorder associated with abnormal cellular interactions (e.g., abnormal cell-cell and/or cell-matrix interactions, abnormal cell migration, movement, e.g., cancer) based on detection of S4BP protein or MRNA. In one embodiment, the method involves contacting a cell or tissue sample (e.g., a biopsy sample) from the subject with an agent capable of detecting S4BP protein or MRNA, determining the amount of S4BP protein or MRNA expressed in the cell or tissue sample, comparing the amount of S4BP protein or mRNA expressed in the cell or tissue sample to a control sample and forming a diagnosis based on the amount of S4BP protein or MRNA expressed in the cell or tissue sample as compared to the control sample. Specific diagnostic tests are described in greater detail below. Kits for detecting S4BP nucleic acid or protein in a biological sample are also within the scope of the invention and are described in greater detail below.

Still another aspect of the invention features methods, e.g., screening assays, for identifying a compound for treating a disorder characterized by aberrant S4BP nucleic acid expression and/or protein activity, e.g., a disorder associated with unwanted or abnormal cellular interactions (e.g., unwanted or abnormal cell-cell and/or cell-matrix interactions, unwanted or abnormal cell migration/movement). These methods typically include assaying the ability of the compound or agent to modulate the expression of the S4BP gene or the activity of the S4BP protein, thereby identifying a compound for treating a disorder characterized by aberrant S4BP nucleic acid expression and/or protein activity. In a preferred embodiment, the method involves contacting a biological sample, e.g., a cell or tissue sample, obtained from a subject having the disorder with the compound or agent, determining the amount of S4BP protein expressed and/or measuring the activity of the S4BP protein in the biological sample, comparing the amount of S4BP protein expressed in the biological sample and/or the measurable S4BP biological activity in the cell to that of a control sample. An alteration in the amount of S4BP protein expression and/or S4BP activity in the cell exposed to the compound or agent in comparison to the control is indicative of a modulation of S4BP expression and/or S4BP activity.

The invention also features methods for identifying a compound or agent which interacts with an S4BP protein. In a preferred embodiment, the interaction with an S4BP protein can be binding, phosphorylation, or otherwise interacting to form or break a bond, e.g., a covalent or non-covalent bond. A compound can include, for example, a fragment or analog of syndecan-4; a polypeptide other than syndecan-4, e.g., a randomly generated polypeptide which interacts with S4BP, or a small molecule. In a preferred embodiment, the method can include the steps of contacting the S4BP protein with the compound or agent under conditions which allow binding of the compound to the S4BP protein to form a complex and detecting the formation of a complex of the S4BP protein and the compound in which the ability of the compound to bind to the S4BP protein is indicated by the presence of the compound in the complex. Methods for identifying a compound or agent can be performed, for example, using a cell free assay. For example, S4BP can be immobilized to a suitable substrate, e.g., glutathione sepharose beads or glutathione derivatized microtitre plates, using a fusion protein which allows for S4BP to bind to the substrate, e.g., a glutathione-S-transferase/S4BP fusion protein.

In another embodiment, a compound or agent which interacts with an S4BP protein can be identified using a cell-based assay. These methods can include identifying a compound or agent based on its ability to modulate, e.g., inhibit or promote, a biological activity of S4BP. In a preferred embodiment, the compound modulates one or more of the following biological activities of S4BP: 1) it interacts, directly or indirectly, with syndecan-4; 2) it interacts, directly or indirectly, with intracellular signaling proteins (e.g., GTP binding protein, focal adhesion kinase, serine-threonine kinase); 3) it interacts, directly or indirectly, with PKCα; 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with paxillin; 6) it modulates actin stress fiber formation and/or organization; 7) it plays a role in an adhesion formation signaling pathway; 8) it modulates cell attachment; 9) it modulates cell spreading.

In another aspect, the invention features methods for identifying compounds which modulate S4BP nucleic acid expression. In a preferred embodiment, nucleic acid expression can be evaluated using a nucleic acid probe, e.g., a labeled probe, capable of hybridizing to an S4BP nucleic acid molecule, e.g., S4BP MRNA. In another preferred embodiment, S4BP nucleic acid expression, e.g., DNA expression, can be evaluated by contacting a compound with an S4BP nucleic acid molecule, e.g., a control region of a S4BP nucleic acid molecule, and evaluating S4BP transcription, in vitro or in vivo. S4BP transcription can be evaluated, for example, by detecting the production of S4BP protein, e.g., using an antibody, e.g., a labeled antibody, or by determining a cell activity, e.g., using a marker gene, e.g., a lacZ gene, fused to the control region of S4BP and following production of the marker.

The invention further features methods for identifying a compound or agent which modulates, e.g., stimulates or inhibits, the interaction of the S4BP protein with a target molecule, e.g., an adhesion receptor (e.g., syndecan-4) or a protein associated with cytoskeleton (e.g., actin, vinculin, paxillin), or a protein involved in a signaling pathway, e.g., a protein involved in adhesion dependent signaling events (e.g., focal adhesion kinase, serine-threonine kinase, GTP binding proteins such as PKCα). In these methods, the S4BP protein is contacted, in the presence of the compound or agent, with the target molecule under conditions which allow binding of the target molecule to the S4BP protein to form a complex. An alteration, e.g., an increase or decrease, in complex formation between the S4BP protein and the target molecule as compared to the amount of complex formed in the absence of the compound or agent is indicative of the ability of the compound or agent to modulate the interaction of the S4BP protein with a target molecule.

A "heterologous promoter", as used herein is a promoter which is not naturally associated with a gene or a purified nucleic acid.

A "purified" or "substantially pure" or isolated "preparation" of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

As used herein, the term "subject" refers to human and non-human animals. In preferred embodiments, the subject is a human e.g., a person having or diagnosed as at risk for having an S4BP related disorder. The term "non-human animals" of the invention includes all vertebrates, e.g., mammals and non-mammals, such as non-human primates, ruminants, birds, amphibians, reptiles.

An "isolated" or "pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA can also includes a recombinant DNA which is part of a hybrid gene encoding sequence.

"Sequence identity or homology", as used herein, refers to the sequence similarity between two polypeptide molecules or between two nucleic acid molecules. To determine the percent homology of two amino acid sequences (e.g., SEQ ID NO:2) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions× 100). For example, if 6 of 10, of the positions in two sequences are matched or homologous then the two sequences are 60% homologous or have 60% sequence identity. By way of example, the DNA sequences ATTGCC and TATGGC share 50% homology or sequence identity. Generally, a comparison is made when two sequences are aligned to give maximum homology or sequence identity.

The comparison of sequences and determination of percent homology between two sequences can be accomplished using a mathematical algorithm. A preferred, non-limiting example of a mathematical algorithm utilized for the comparison of sequences is the algorithm of Karlin and Altschul Proc. Natl. Acad. Sci. USA 87:2264–68, 1990, modified as in Karlin and Altschul Proc. Natl. Acad. Sci. USA 90:5873–77, 1993. Such an algorithm is incorporated into the NBLAST and XBLAST programs (version 2.0) of Altschul, et al. J Mol. Biol. 215:403–10, 1990. BLAST nucleotide searches can be performed with the NBLAST program, score=100, wordlength-12 to obtain nucleotide sequences homologous to S4BP nucleic acid molecules of the invention. BLAST protein searches can be performed with the XBLAST program, score=50, wordlength=3 to obtain amino acid sequences homologous to S4BP protein molecules of the invention. To obtain gapped alignments for comparison purposes. Gapped BLAST can be utilized as described in Altschul et al., Nucleic Acids Res. 25(17):3389–3402, 1997. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The terms "peptides", "proteins", and "polypeptides" are used interchangeably herein.

A "biological activity of S4BP" refers to one or more of the following activities: 1) it interacts, directly or indirectly, with syndecan-4; 2) it interacts, directly or indirectly, with intracellular signaling proteins (e.g., GTP binding protein, focal adhesion kinase, serine-threonine kinase); 3) it interacts, directly or indirectly, with PKCα; 4) it modulates cytoskeletal organization, e.g., it modulates the interaction of a matrix receptor (e.g., syndecan-4) and intracellular proteins associated with cytoskeleton (e.g., actin, vinculin); 5) it interacts, directly or indirectly, with paxillin; 6) it modulates actin stress fiber formation and/or organization; 7) it plays a role in an adhesion formation signaling pathway; 8) it modulates cell attachment; 9) it modulates cell spreading.

The term "small molecule", as used herein, includes peptides, peptidomimetics, or non-peptidic compounds, such as organic molecules, having a molecular weight less than 2000, preferably less than 1000.

As used herein, the term "transgene" means a nucleic acid sequence (encoding, e.g., one or more subject S4BP polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as mammary tissue. The term also covers so-called "leaky" promoters, which regulate expression of a selected DNA primarily in one tissue, but cause expression in other tissues as well.

"Unrelated to an S4BP amino acid or nucleic acid sequence" means having less than 30% sequence identity, less than 20% sequence identity, or, preferably, less than 10% homology with a naturally occurring S4BP sequence disclosed herein.

A polypeptide has S4BP biological activity if it has one or more of the properties of S4BP disclosed herein. A polypeptide has biological activity if it is an antagonist, agonist, or super-agonist of a polypeptide having one of the properties of S4BP disclosed herein.

"Misexpression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. As described herein, one aspect of the invention features a substantially pure (or recombinant) nucleic acid which includes a nucleotide sequence encoding an S4BP polypeptide and/or equivalents of such nucleic acids. The term nucleic acid as used herein can include fragments and equivalents. The term equivalent refers to nucleotide sequences encoding functionally equivalent polypeptides. Equivalent nucleotide sequences will include sequences that differ by one or more nucleotide substitutions, additions or deletions, such as allelic variants, and include sequences that differ from the nucleotide sequences disclosed herein by degeneracy of the genetic code.

As used herein, the term "hybridizes under stringent conditions" refers to conditions for hybridization and washing under which nucleotide sequences typically remain hybridized to each other. Preferably, the conditions are such that sequences which have at least about 60%, at least about 65%, more preferably at least about 70%, and even more preferably at least about 75% or more sequence identity to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred example of stringent hybridization conditions are hybridization in 6x sodium chloride/sodium citrate (SSC) at about 45° C., followed by one or more washes in 0.2xSSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural S4BP protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIGS. 1A–B depicts the cDNA sequence and predicted amino acid sequence of chicken S4BP. The nucleotide sequence corresponds to nucleic acids 1 to 1182 of SEQ ID NO:1. The amino acid sequence corresponds to amino acids 1 to 320 of SEQ ID NO:2.

DETAILED DESCRIPTION

The present invention is based on the discovery of novel molecules, referred to herein as S4BP nucleic acid and protein molecules, which play a role in cell matrix interactions. In one embodiment, the S4BP molecules modulate proteins involved in cytoskeletal organization. In a preferred embodiment, the S4BP molecules of the invention are capable of modulating interactions between the matrix receptor syndecan-4 and intracellular proteins associated with cytoskeleton such as actin, vinculin and/or paxillin.

S4BP was found to interact with the cytoplasmic domain of syndecan-4. The binding of S4BP to the cytoplasmic domain of syndecan-4 is direct and specific and involves both the highly conserved membrane proximal and the variable central region of this domain. Although the conserved membrane proximal domain alone is able to mediate the interaction of syndecan-4 with S4BP, the central variable domain appears to confer specificity to the interaction. The involvement of the central domain as a mediator of this specificity is indicated from three observations. First, S4BP does not bind to the cytoplasmic domains of any of syndecan-1, 2 or 3, even though these cytoplasmic domains contain conserved membrane proximal and C-terminal sequences that are identical to the cytoplasmic domain of syndecan-4. Second, the membrane proximal domain alone shows diminished binding relative to the intact cytoplasmic domain. Finally, an internal deletion of the central variable domain abolishes binding.

The S4BP proteins or polypeptides of the invention can also interact with proteins associated with cytoskeleton such as actin. Preferably, the S4BP protein or polypeptide interacts with proteins of the cytoskeleton through an adhesion dependent signaling pathway. It was found that overexpression of S4BP on cell morphology was more pronounced during the initial stages of cell adhesion and spreading. In addition, cells in the absence of serum further enhanced the phenotype. These observations suggest that the regulation of cell morphology by S4BP is independent of serum and requires an adhesion dependent signal. The ability of S4BP to regulate actin stress fiber formation and organization suggests a function parallel to downstream serum dependent pathways. S4BP localization to focal contacts, alignment with actin fibrils and basal distribution suggests a potential function as a bridging molecule between extracellular matrix receptors and the cytoskeleton. Thus, in one aspect the invention features S4BP proteins and polypeptides which bind to syndecan-4 and/or mediate interaction between adhesion receptor, syndecan-4 and proteins associated with cytoskeleton.

Isolation and Cloning of S4BP cDNA

To identify and characterize proteins that might interact with the cytoplasmic domain of syndecan-4, a yeast interactive trap system in which the cytoplasmic domain of syndecan-4 was used as bait. See Finley and Brent (1994) and Zervos et al. (1993) *Cell* 72:223–232. The yeast strain EGY48 MATa trpl ura3 LEU2:pLexAop6-LEU2 was used as host. The reporter plasmid pSH18-34 was used for the b-D-galactoside (X-gal) assay. The bait plasmid was constructed by fusing the nucleotide sequence that encodes amino acids 169 through 197 of the cytoplasmic domain of avian syndecan-4 in frame with the nucleotide sequence of the LexA DNA binding domain and C-terminal dimerization domain in pLexA202+PL2 (LexA-CS4C). The target library for the screen was a 4 day chick embryonic limb bud cDNA library made in plasmid pJG 4–5. Control baits for the screen were LexA-n-myc, LexA-R4CK230R, LexA-Cyclin C (Zervos et al. (1993) and Wang et al. (1994). Plasmids pSH18–34 and LexA-CS4C were introduced in EGY48 and maintained under selection for the URA3 and HIS3 markers. This strain was then transfected with the 4 day chick embryonic limb bud cDNA library. An estimated $0.5 \times 10^6$ unique yeast clones were selected on Ura-His-Trp-glucose plates, scraped and pooled and stored $-70°$ C. Approximately, $5 \times 10^6$ clones from the amplified yeast stock were screened for potential interactors on Ura-His-Trp-Leu-galactose plates. Positive colonies were then streaked on Ura-His-Trp-X-gal galactose and on Ura-His-Trp-X-gal glucose plates. Colonies that grew on Ura-His-Trp-Leu-galactose and produced blue colonies on Ura-His-Trp-X-gal glucose plates only were isolated and introduced into KC8 cells. Isolated cDNAs were characterized by restriction and sequence analysis and tested for specificity of the interaction on control baits mentioned above.

Sequence analysis of clones which specifically interacted with the cytoplasmic domain of syndecan-4 in the yeast two-hybrid screen, identified a novel partial cDNA that encoded a unique polypeptide sequence with limited sequence homology to MEK-1. Using the partial cDNA to screen a LMH (Baciu et al. (1994) *J. Biol. Chem.* 269:696–703) and an avian embryonic cDNA library (Clontech, Palo Alto, Calif.), several full length clones were isolated and sequenced. All clones shared a common large open reading frame initiated at a cluster of four methionine residues. The encoded polypeptide sequence of in the C-terminal region in the identified full length clone was identical to that of the initial partial cDNA isolated in the two-hybrid screen. The full length cDNA identified is referred to as S4BP and the encoded S4BP protein used in an in vitro binding assay (see below) to confirm the interaction. The nucleotide and amino acid sequences of S4BP are shown in SEQ ID NO:1 and SEQ ID NO:2, respectively, and in FIG. 1.

A comparison of the S4BP sequence to those in the Genbank database identifies S4BP as a novel protein and the predicted polypeptide identifies no large regions of homology with polypeptide sequences present in that database. However, a motif search revealed several subdomains in the protein that show homology to known protein motifs. As indicated below, following the second and third methionine residues are glycine residues that conform to the myristoylation motif (Tower (1987) *J. Biol. Chem.* 262:1030–1036). The Pro-Pro-Leu-Pro sequence (amino acids 24–27) in the N-terminal domain satisfies the requirement for an SH3 domain binding site motif(Feng et al. (1994) *Science* 266:1241–1247). Within the central portion of S4BP amino acids 190–199 show limited homology with the activation loop of MEK-1 (Hardie and Hanks (1995) *The protein kinase facts book*, Academic Press Inc. Additional homology is seen for relative positions of amino acids Asp-His-Gly (residues 162–164) and Pro-Glu (residues 212–213) with Asp-Phe-Gly in subdomain VII and Pro-Glu in subdomain VIII of MEK-1. No additional homology to either MEK or other eukaryotic kinases was found.

In Vitro Transcription-Translation Assay

In vitro transcription-translation was carried out using the TNT in vitro transcription-translation kit from In Vitrogen Inc. (San Diego, Calif.). Reactions were carried out as described by the manufacturer. For initial analysis, S4BP cDNA was subcloned into pcDNA 3.0 (In Vitrogen) and the T7 promoter used for RNA synthesis. Control reactions were carried out in the presence and absence of vector without insert. Specificity of product was verified by western analysis of in vitro transcription-translation product. For analysis of methionine start sites, individual PCR products were generated using 5' primer containing T7 promoter sequence and nucleotides 1–30. To examine individual initiation methionines, nucleotides corresponding to the individual methionine residues were mutated to GTG. 3' primers corresponded to NT 1079 to 1099. PCR products were generated using Extend PCR Polymerase mix (Boehringer, Mannheim). The resulting PCR products were purified and used in the in vitro translation-transcription reaction. Control reactions were done using no PCR product or PCR product in which the T7 promotor was linked with a primer corresponding to NT 3' to the initiation codons (NT 31–51).

In vitro transcription-translation analyses using the full-length clone subcloned in to pcDNA 3.0 (LMH4A) identified a 40 kDa band as the principal translation product. Deletion of the 5' nucleotides from −12 to +30 blocked all protein synthesis implicating the cluster of methionine residues encoded by nucleotides 1 through 30 of SEQ ID NO:1 as the initiation site. The 40 kDa polypeptide obtained in in vitro transcription-translation experiments was recognized by an anti-S4BP polyclonal antibody and corresponds in molecular weight to a band identified in tissue extracts from avian embryonic tissues.

To determine the initiation methionine which is used in the cluster of four potential initiation sites encoded by nucleotides 1 through 30, directed mutational and in vitro transcription-translation analyses were used. Mutations in which only one of the four potential initiation codons is left intact or in which individual initiation codons are abolished, indicate that translation can be initiated at any of the four methionine residues. The methionine residues encoded by the second and third potential initiation codons are followed by a glycine residue which provides the structural requirements for myristoylation of S4BP (Towler et al. (1987) *J. Biol. Chem.* 262:1030–1036). The identification of myristoylation of S4BP (see below) indicates that initiation in vivo is likely to occur at either the second or third methionine residue. However, the second site shows the greatest homology to the GCCGCC(A/G)CCAUGG (SEQ ID NO:7) Kozak consensus sequence (Kozak (1987) *Nucl. Acid Res.* 26:8125–8148) relative to the third initiation site, suggesting that, in vivo initiation at the second methionine is likely to be favored.

Analysis of S4BP Expression

Western analysis: Tissues from 8 day chicken embryos were solubilized in 4×SDS-PAGE sample buffer at 20 mg of wet tissue/50 μl of buffer, boiled and frozen. Before use, they were thawed and homogenized using a 21 gauge needle. Five μl samples were loaded on a 10% SDS-PAGE gel, electrophoresed and blotted onto an Iuuobilon-P membrane. Protein was visualized using affinity purified anti-S4BP polyclonal antibodies (see immunocytochemistry section) followed by anti-rabbit HRP conjugated secondary antibodies (Biorad, Hercules, Calif.) and ECL substrate (NEN Life Science Products, Boston, Mass.).

Western blot analysis with anti-S4BP polyclonal antibodies reveals a single 40 kDa polypeptide in 8 day chick embryonic brain, eyes, gizzard, heart, intestine, kidney, liver, tibia and skin.

Northern analysis: RNA was isolated from chicken embryonic tissues using the isothiocyanate method as described in Sambrook et al. (1989) *Molecular Cloning: A Laboratory Manual*, Cold Spring Harbor Press, Cold Spring Harbor, N.Y. Ten μg of total RNA from each tissue were separated on a 1.5% agarose formamide gel and blotted onto an Immobilon-N membrane (Millipore, Bedford, Mass.). The resulting blot was blocked for 4 hours at 62° C. in 6×SSC, 5×Denhardt solution containing 0.5% SDS and 100 μg/ml sheared salmon sperm DNA. Fifty ng of purified insert from clone LMH4A was randomly labeled with dCTP-[$^{32}$P] using random primers and Klenow fragment (Pharmacia, Uppsala, Sweden). Approximately $10^6$ dpm/ml in a final volume of 10 ml was used to probe the blotted mRNA. After hybridization, the membranes were washed at high stringency according to the manufacturer's instructions and exposed to X-Omat film (Kodak, Rochester, N.Y.). Molecular weights were estimated using RNA standards from Life Technologies (Gaithersburg, Md.).

Northern analysis indicates the presence of three mRNAs of 2.1, 1.7 and 1.5 kb. The smaller transcript corresponds to alternate poly-A addition sites as determined by sequence analysis. All three species of MRNA are observed in aorta, heart, brain, gizzard, kidney, liver, proventriculus and skin from ten day old embryonic tissues and in intestine and muscle from 15 day old embryos.

Myristoylation Assay

CEFs (70% confluent) were labeled for 24 hours with 1 mCi of [9,10(n)-3H] Myristic acid (Amersham) in 5 ml DMEM supplemented with 10% dialyzed FBS. Cells were lysed in RIPA buffer and proteins were immunoprecipitated with a rabbit preimmune serum, a rabbit anti-S4BP antibody or a mouse monoclonal anti-src antibody (Upstate Biotechnology) as a positive control for myristoylation. After immunoprecipitation, the proteins were run on an 12% SDS-PAGE, transferred to Immobilon-P and examined for radioactive proteins by autoradiography for 21 days as described in Mumby and Buss (1990) *Methods: A Companion to Methods in Enzymology* 1:216–220.

The second and the third methionine residues in the cluster of the four potential initiation sites are followed by glycine residues. If translation were initiated at these methionine residues, the glycine residues that follow them could be myristoylated. Direct tests of the possible myristoylation of S4BP were carried out in CEF cultures. Subconfluent CEFs were labeled in vivo with of $^3$H-myristic acid and cell extract prepared and immunoprecipitated with anti-S4BP antibodies. The resulting immunoprecipitates were electrophoresed on SDS-PAGE and transferred to Immobilon-P and examined for $^3$H-labeled S4BP, by autoradiography. Src, a known myristoylated protein, was immunoprecipitated from the same extract with anti-src antibodies and analyzed in the same manner as S4BP as a positive control. After autoradiography, a single band with the predicted molecular weight of 40 kDa for S4BP was found in the S4BP immunoprecipitate. A single band was also identified in the src immunoprecipitate with the predicted molecular weight of 60 kDa of this protein.

To examine the in vivo association of S4BP with syndecan-4, an immunoprecipitation assay was also carried out using affinity purified anti-syndecan-4 (CS4E), anti-S4BP polyclonal antibodies or pre-immune IgG. Equivalent amounts of total protein lysates from chick embryo fibroblasts were immunoprecipitated using each of the indicated antibodies. Immunoprecipitates were separated on a 10% reducing SDS-PAGE gel and western blotted using affinity purified anti-S4BP polyclonal antibodies. The presence of a 40 kDa reactive band in the whole cell lysate, anti-S4BP and anti-syndecan-4 immunoprecipitations, and not from the pre-immune IgG, indicates in vivo association of S4BP with syndecan-4. 100941 These results indicate that S4BP can be myristoylated. It may be that all, or only a fraction, of S4BP is myristoylated. Myristoylation of S4BP suggests directed localization of S4BP to the plasma membrane and is in keeping with the observed localization of S4BP within the basal membrane. Stable anchoring of proteins to membranes usually involves two points of attachment involving a combination of myristoylation-palmitoylation flanked by basic amino acids (Resh (1994) Cell 76:411–413). The membrane anchoring effect of the basic amino acids results from an interaction with the acidic membrane phospholipids. S4BP does not have the basic amino acids immediately following either of the two potentially myristoylated glycine residue that could interact with the membrane phospholipids. Since S4BP interacts with the cytoplasmic domain of syndecan-4, the second point of membrane attachment for S4BP may be syndecan-4.

Bacterial Expression cDNAs encoding complete or various mutant forms of syndecan-4 or S4BP were cloned in frame with either glutathione transferase using PGEX 5X-2 (Pharmacia, Uppsala, Sweden) or maltose binding protein using pMAL-C2 (NE Biolabs, Beverly, Mass.) expression vectors. Ligated plasmids were initially transfected in Sure cells (Stratagene, La Jolla, Calif.) and clones were verified by sequence analysis and analyzed for expression by SDS-PAGE. For protein expression, cDNAs, transfected into Sure cells for propagation, were transfected into BL-21 cells (Novagen, Madison, Wis.). Protein expression was accomplished by growing the transfected cells to an O.D.$_{600}$ of 0.6 in high growth medium followed by a 1–2 hour induction period using 1 mM IPTG (Sigma, St Louis, Mo.). At the end of the incubation period, cells were pelleted and resuspended in lysis buffer pH 7.5 (15 mM sodium phosphate, 30 mM NaCl, 0.25% Tween 20, 10 mM EDTA, 10 mM EGTA, 2 $\mu$g/ml lysozyme and protease inhibitors cocktail (Complete™, Boehringer Mannheim). Cells were lysed by sonication for 1 minute on ice using a microtip probe at a setting of 5 at 50% duration (Branson). Insoluble material was removed by centrifugation at 14,000×g for 10 minutes. Expressed proteins were either passed over a maltose affinity column (NE Biolabs, Beverly, Mass.) for pMal fusion proteins or over a glutathione affinity column for GST-fusion proteins. After binding and in preparation for elution, the columns were extensively washed with lysis buffer, followed by a lysis buffer wash that contained 0.5 M NaCl and equilibrated in phosphate buffer. pMal fusion proteins were eluted in lysis buffer containing 10 mM maltose. GST-S4BP fusion proteins remained bound to the GST affinity matrix for protein binding assays.

In Vitro Binding Assay

Whereas the co-immunoprecipitations demonstrate in vivo associations, they do not demonstrate a direct association of S4BP with the cytoplasmic domain of syndecan-4, nor do they indicate a specificity of S4BP for syndecan-4. To address both the direct interaction of S4BP with syndecan-4 and its specificity, an in vitro binding assay was performed in which bacterially expressed GST-S4BP fusion protein was immobilized on glutationine agarose beads and assayed for its ability to bind soluble purified pMal/syndecan-4 fusion proteins.

Fifteen $\mu$l of a 50% slurry of GST-S4BP bound to GST beads were incubated with 10 $\mu$g of soluble pMal-syndecan in 0.5 ml of lysis buffer that contained 1% BSA. After incubation for 30 minutes at room temperature with constant mixing, the reaction mixtures were placed on ice and washed 3× with lysis buffer followed by, 3 washes with lysis buffer containing 1 M NaCl. Protein bound to GST-S4BP beads was solubilized in SDS-PAGE buffer, electrophoresed, transferred to an Immobilon-P membrane and analyzed for bound syndecan-4 core protein using the avian specific syndecan-4 polyclonal antibody CS4E (Baciu et al. (1994) *J. Biol. Chem.* 269:696–703).

Full length syndecan-4 core protein (S-4), but not a cytoplasmic deletion mutant (Tailless) binds S4BP. That the interaction is between S4BP and not GST is evident from the lack of binding of full length syndecan-4 with GST alone. These analyses indicate that the interaction of syndecan-4 core protein with S4BP results from a direct interaction with the cytoplasmic domain of syndecan-4.

The specificity of the interaction for the cytoplasmic domain of syndecan-4 was then examined. For this analysis, chimeric proteins were constructed in which the cytoplasmic domain of syndecan-4 was replaced with the cytoplasmic domains of either syndecan-1, -2 or -3 in the full length syndecan-4 pMal construct. S4BP interacts specifically with the cytoplasmic domain of syndecan-4 (S-4) and not with any of the chimeric core proteins in which the cytoplasmic domain of syndecan-4 had been replaced with that of syndecan-1 (S-1), syndecan-2 (S-2) or syndecan-3 (S-3). These results indicate that the interaction of S4BP is specific for the cytoplasmic domain of syndecan-4 and they suggest that amino acids unique to the cytoplasmic domain of syndecan-4 mediate that interaction.

To identify amino acids in the cytoplasmic domain of syndecan-4 that mediate the interaction of syndecan-4 with S4BP, a series of cytoplasmic deletion mutants were generated and tested for their ability to interact with immobilized GST-S4BP. No binding between full length syndecan-4 and GST could be detected relative to the binding of full length syndecan-4 with GST-S4BP. Removal of amino acids 197 through 180 from the carboxyl-terminus through the central domain of the cytoplasmic domain diminished, but did not abolish, binding of syndecan-4 to S4BP. The removal of the final membrane proximal amino acids abolished all binding. These results suggest that the conserved membrane proximal region is essential for binding and that the variable central and conserved C-terminal regions affect the degree of interaction. To test the involvement of both the conserved membrane proximal region and the variable central regions of the cytoplasmic domain in the binding of S4BP, internal deletions for the central and the membrane proximal domains were generated. In both instances, the internal deletion mutant constructs had no specific interaction with GST-S4BP in the binding assays. The data from the deletion constructs, coupled with the observation that S4BP interacts only with the cytoplasmic domain of syndecan-4 and not with that of other family members suggest that both the membrane proximal and central variable region of the cytoplasmic domain are involved in the interaction with S4BP.

The observation that the specific interaction of S4BP with the cytoplasmic domain of syndecan-4 involves both the membrane proximal portion that is shared by all syndecan family members and the central variable region that is unique for this family member, suggests that analogous interactions may occur involving the cytoplasmic domains of syndecan-1, -2 and -3 and proteins that may make up a family of S4BP related proteins. Interaction with individual S4BP family members could occur through their ability to recognize the proximal amino acids while adjacent amino acids in the central variable domain could confer specificity of binding. A possible example of such binding may be found in the interactions of the cytoplasmic domain of syndecan-3 with a protein complex that contains Src family kinases and the substrate cortactin as well as a 30 kDa protein (Kinnunen et al. (1998) *J. Biol. Chem.* 273:10702–10708). These interactions could be competed with a synthetic peptide with the sequence of the conserved membrane proximal region of the cytoplasmic domain. It was not reported if the binding of the protein complex was specific for the cytoplasmic domain of syndecan-3 or if it could also bind the cytoplasmic domains of syndecan-1, -2 and -4. If the interaction were specific for the cytoplasmic domain of syndecan-3, one might expect an involvement of the central variable region in a manner similar to the one reported here for S4BP and the cytoplasmic domain of syndecan-4. A general interaction of proteins with all syndecan cytoplasmic domains has been reported involving the highly conserved C-terminal amino acids and the PDZ-domain containing proteins, syntenin (Grootjans et al. (1997) *Prot. Natl Acad. Sci. USA* 94:13683–13688), and CASK/LIN-2 (Cohen et al. (1998) *J. Biol. Cell* 142:129–138; Hsueh et al. (1998) *J. Cell. Biol.* 142:139–151). Thus, both general or specific interactions between the cytoplasmic domains of the syndecan family members and cytoplasmic proteins can be envisaged depending on whether the binding involves the highly conserved regions or the variable regions. These multiple interactions may be possible as a result of the oligomerization of syndecans (Carey (1997) *Biochem. J.* 327:1–16) or they may occur in a sequential manner. Alternatively, these multiple associations may occur in a tissue dependent manner in which a single syndecan may perform different functions.

Interactions Between S4BP, PKC and Paxillin

Protein kinase C (PCK) activation with phorbol ester, 12-0-tetradecanoylphorbal 13-acetate (TPA) in serum starved chicken embryo fibroblasts (CEFs) triggers a number of interactions between syndecan-4, PKCα, S4BP and paxillin. These interactions were observed in co-immunoprecipitation experiments during the first five minutes following TPA treatment. First, S4BP interacts with PKCα. This is a relatively short lived interaction which is followed by the interaction of S4BP with syndecan-4. TPA also triggers an interaction between S4BP and paxillin in serum starved cells. An interaction between S4BP and paxillin was also demonstrated in co-immunoprecipitation experiments from normal non-serum starved CEFs. The interaction between S4BP and paxillin is direct as indicated from experiments in which S4BP was radiolabeled in in vitro transcription/translation reactions binds to GST-paxillin but not to GST alone as a negative control. His-5 is a focal adhesion protein that is closely related to paxillin and is present in WFB rat fibroblast cells. GST-His-5 also binds radiolabeled S4BP generated in in vitro transcription/translation reactions. These molecular interactions connect syndecan-4 with the cytoskeletal protein paxillin, and therefore, place this proteoglycan in a signaling pathway which regulates actin cytoskeletal organization and focal adhesion formation.

Cell Culture

Primary chicken embryo fibroblasts (CEF) were obtained from dorsal skins of eight day old embryos as described in Baciu et al. (1994) *J. Biol. Chem.* 269:696–703. NIH 3T3 cells were obtained from ATCC (Cat# CRL 1658). Both cell types were maintained at subconfluent densities in Dulbecco's Modified Eagles Medium (DMEM) supplemented with 10% fetal bovine serum (FBS), streptomycin (250 $\mu$g/ml) and penicillin (250 units/ml) (Life Technologies, Gaithersburg, Md.) in a humidified atmosphere at 37° C. For serum deprivation experiments, cells were cultured for 16 to 18 hours in medium containing only DMEM and antibiotics prior to trypsinization and replating.

For transfection experiments cells were plated in six well tissue culture plates (Falcon, Bedford, Mass.) at $2.5 \times 10^5$ cells per well and cultured overnight in complete growth medium. The cells were then washed once in serum free DMEM and transfected with 2 $\mu$g of circular plasmid DNA using 5 $\mu$l of Lipofectin (Life Technologies, Gaithersburg, Md.) in 1 ml of serum free DMEM. After 5 hours, the transfection medium was replaced by complete growth medium. To obtain stable NIH 3T3 transformants cDNAs were cloned into the pcDNA 3.0 vector (In Vitrogen, Carlsbad, Calif.). Forty eight hours after transfection, the cells were plated into three 150 mm dishes and selected for G418 resistant growth (700 $\mu$g/ml) for 10 days. At this point, individual colonies were cloned with cloning rings (Specialty Media Inc., Lavalette, N.J.), expanded and frozen stocks were prepared. Clones expressing the transgene products were characterized by western analysis and immunocytochemistry.

Immunocytochemistry

Cells were fixed according to the procedure of Woods and Couchman (1994) *Mol. Biol. Cell* 5:183–192, and stained as described in Baciu and Goetinck (1995) *Mol. Biol. Cell* 11:1503–1513. The polyclonal antibodies used in these studies were directed against a unique amino acid sequence of the ectodomain of avian syndecan-4 (CS-4-E) and against S4BP. The generation and affinity purification of CS-4-E has been described (Baciu et al. (1994) *J. Biol. Chem.* 269:696–703). Affinity purified CS-4-E was used at a concentration of 20 $\mu$g/ml. Anti-S4BP were generated in rabbits using a pMal-S4BP fusion protein as an immunogen. Anti-S4BP antibodies were affinity purified initially by passing the immune serum over a pMal-S4BP-CL-4B affinity column. Bound antibodies were eluted with 0.1 M glycine, pH 2.5 and neutralized with 1/10 vol. 1 M tris pH 8.0. Antibodies that recognize the maltose binding protein were eliminated by chromatography on a maltose binding protein-CL-4B affinity column. The specificity of the reactivity of the resulting antibodies was verified by western blot analysis of GST-S4BP and pMal-syndecan fusion proteins. The vinculin (VN 3–24) monoclonal antibody (Gardener and Fambrough (1983)) was obtained from the Developmental Studies Hybridoma Bank maintained by the Department of Pharmacology and Molecular Sciences, John Hopkins University School of Medicine, Baltimore, Md. 21205, and the Department of Biological Sciences, University of Iowa, Iowa City, Iowa 52242, under contract N01-HD-2-3244 from the NICHD. The monoclonal antibody was from ascites fluid and used at a 1/100 dilution. FITC-phalloidin (Molecular Probes, Eugene, Oreg.) was used for actin staining according to the manufacturer's instructions. To visualize primary antibody staining, the slides were incubated with a 1/75 dilution of either TRITC conjugated or FITC conjugated secondary antibodies (Pierce, Rockford, Ill.) for 30 minutes at room temperature. The secondary antibodies are identified in the figure legends. After washing three times with PBS, cover slips were mounted using Flouromount G (Biomedia, Foster City, Calif.). Immunocytochemical analysis was carried out using a Leica Confocal microscope. Of the three emission channels used during multiple labeling experiments, excitation levels and gain were set to eliminate bleed-through from one channel to the other as outlined by the manufacturer. This was verified experimentally. Non-specific staining was determined by use of secondary antibody alone.

Quantitation of Cell Spreading

Images of actin stained NIH 3T3 cells were captured using a Nikon E800 microscope using epifluorescence and Spot digital camera (Diagnostic Instruments, Sterling Heights, Mich.). Quantitation of cell surface area was measured using the ImagePro Plus image analysis system (Mediacybernetics, Silver Spring, Md.). Values represent means and standard deviations of the means from the analysis of 90 cells obtained at random from each sample.

As discussed above, NIH 3T3 cells were transfected with either the pcDNA 3.0 expression vector, as a control, or with the pcDNA 3.0 vector that harbors the avian S4BP cDNA. Expression of S4BP was verified by western analysis. The control transfectant clone, which shows no expression of avian S4BP, was compared with three transfected clones that express different levels of S4BP for possible syndecan-4 associated effects on cell morphology, actin stress fiber and focal contact formation. No significant differences in cell morphology could be detected between S4BP expressing and control NIH 3T3 cells plated overnight on fibronectin coated slides in the presence of serum. Occasionally, a tendency for enhanced spreading was observed in cells overexpressing S4BP cultured under these conditions. However, when serum deprived cells were allowed to adhere and spread on fibronectin coated slides in the absence of serum, the S4BP expressing cells showed a clear enhancement in cell surface area and in actin stress fiber and focal contact formation (Figure). The control and the three S4BP expressing clones had an average surface area of 353 (+/−172), 635 (+/−265), 581 (+/−205) and 589 (+/−236) $\mu m^2$ (Mean +/−S.D.), respectively. This represents an increase of 77, 62, and 65% in total cell surface area of the S4BP expressing clones, respectively, with respect to the control clone. Furthermore, an enhancement in filopodia formation was observed in the two clones that expressed higher levels of S4BP. The effect of S4BP expression on cell spreading and on actin stress fiber and focal contact formation was greatly diminished when cells were plated in the presence of serum or if they were not serum starved before trypsinization. This observation suggests an adhesion dependent regulation of actin stress fiber formation and cell spreading by S4BP.

The ability of S4BP to mediate cell spreading and actin reorganization is in keeping with functional characterization of syndecan family members as mediators of cell morphology and cytoskeletal organization (Vainio et al. (1991) Dev. Biol. 147:322–333; Carey et al. (1994) J. Cell Biol. 124:161–170; Kato et al. (1995) Mol. Biol. Cell 6:559–576; Kinnunen et al. (1998) J. Biol. Chem. 273:10702–10708). The effect of overexpressing S4BP on cell morphology was more pronounced during the initial stages of cell adhesion and spreading than in cultures which had been plated for 24 hours. Plating cells in the absence of serum further enhanced the phenotype. These observations suggest that the regulation of cell morphology by S4BP is independent of serum and requires an adhesion dependent signal. This signal may be reflected in the formation of filopodia, which were frequently observed in cells that overexpressed S4BP. The ability of S4BP to regulate actin stress fiber formation suggests a function parallel to downstream from serum dependent pathways. Its localization to focal contacts, alignment with actin fibrils and basal distribution suggests a potential function as a bridging molecule between ECM receptors and the cytoskeleton.

The predominant staining pattern for S4BP is a punctate pattern with an association with focal contacts and along actin stress fibers. Its association with focal contacts appears to be most evident during the initial stages of cell adhesion and focal contact formation when pronounced F-actin staining is also observed. Later in the spreading process or in fully spread cells, low levels of S4BP staining are observed in focal adhesions. However, the predominant staining is in a punctate pattern along the basal cell surface. This punctate staining pattern suggests that S4BP may provide an association of actin fibrils with points of cell matrix association outside of classically defined focal contacts. This pattern of staining contrasts to that observed for syndecan-4 which shows pronounced focal contact staining, especially in well spread cells that correlate with active sites of matrix assembly. The discrepancy between the subcellular detection of syndecan-4 and S4BP may reflect the inability of the antibody to recognize S4BP in fully established focal contacts. Alternatively, the subcellular association of S4BP with focal contacts or the cytoskeleton may be a dynamic process that may change depending on the physiological state of the cells or on cell type. The proposed dynamic role of S4BP may also be dependent on its state of myristoylation. Together, these observations suggest that the interaction of syndecan-4 and S4BP may occur early after adhesion or outside of the classical focal contact in events that lead to focal contact formation. The punctate staining pattern observed for both syndecan-4 and S4BP would be consistent with such a role.

Analogs of S4BP

Analogs can differ from naturally occurring S4BP in amino acid sequence or in ways that do not involve sequence, or both. Non-sequence modifications include in vivo or in vitro chemical derivatization of S4BP. Non-sequence modifications include changes in acetylation, methylation, phosphorylation, carboxylation, or glycosylation.

Preferred analogs include S4BP (or biologically active fragments thereof) whose sequences differ from the wild-type sequence by one or more conservative amino acid substitutions or by one or more non-conservative amino acid substitutions, deletions, or insertions which do not abolish the S4BP biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Gene Therapy

The gene constructs of the invention can also be used as apart of a gene therapy protocol to deliver nucleic acids encoding either an agonistic or antagonistic form of an S4BP polypeptide. The invention features expression vectors for in vivo transfection and expression of an S4BP polypeptide in particular cell types so as to reconstitute the function of, or alternatively, antagonize the function of an S4BP polypeptide in a cell in which that polypeptide is misexpressed. Expression constructs of S4BP polypeptides, may be administered in any biologically effective carrier, e.g. any formulation or composition capable of effectively delivering the S4BP gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO$_4$ precipitation carried out in vivo.

A preferred approach for in vivo introduction of nucleic acid into a cell is by use of a viral vector containing nucleic acid, e.g. a cDNA, encoding an S4BP polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Arnentano et al. (1990) *Proc. Natl. Acad. Sci. USA* 87:6141–6145; Huber et al. (1 991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an S4BP polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject S4BP gene by the targeted cell. Exemplary gene delivery systems of this type include liposomal derived systems, poly-lysine conjugates, and artificial viral envelopes.

In a representative embodiment, a gene encoding an S4BP polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic S4BP gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Transgenic Animals

The invention includes transgenic animals which include cells (of that animal) which contain an S4BP transgene and which preferably (though optionally) express (or misexpress) an endogenous or exogenous S4BP gene in one or more cells in the animal. The S4BP transgene can encode the wild-type form of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns, e.g., to restrict production to the milk or other secreted product of the animal.

Production of Fragments and Analogs

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to other S4BP subunits, assembly into a trimeric S4BP molecules, binding to natural ligands or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays such as the system described above (as with the other screening methods described herein), can be used to identify fragments or analogs (see e.g., U.S. Pat. No. 5,283,317; PCT publication WO94/10300; Zervos et al. (1993) Cell 72:223–232; Madura et al. (1 993) J Biol Chem 268:12046–12054; Bartel et al. (1993) Biotechniques 14:920–924; and Iwabuchi et al. (1993) Oncogene 8:1693–1696). These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., an S4BP molecule or a fragment thereof. The second hybrid protein contains a transcriptional activation domain fused to a "fish" protein, e.g. an expression library, e.g., an embryonic limb bud expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387–392), PhoE (Agterberg, et al. (1990) Gene 88, 37–45), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxyl termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the MRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject S4BP polypeptides to generate mimetics, e.g. peptide or non-peptide agents. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffrnan et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), ketomethylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Antibodies

The invention also includes antibodies specifically reactive with a subject S4BP polypeptides. Anti-protein/anti-peptide antisera or monoclonal antibodies can be made as described herein by using standard protocols (See, for example, *Antibodies: A Laboratory Manual* ed. by Harlow and Lane (Cold Spring Harbor Press: 1988)).

Antibodies which specifically bind S4BP epitopes can also be used in immunohistochemical staining of tissue samples in order to evaluate the abundance and pattern of expression of S4BP. Anti-S4BP antibodies can be used diagnostically in immuno-precipitation and immunoblotting to detect and evaluate S4BP levels in tissue or bodily fluid as part of a clinical testing procedure.

Another application of antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxyl termini consist of a foreign polypeptide. Antigenic epitopes of a subject polypeptide can then be detected with antibodies, as, for example, reacting nitrocellulose filters lifted from infected plates with antibodies of the invention. Phage, scored by this assay, can then be isolated from the infected plate. Thus, the presence of homologs can be detected and cloned from other animals, and alternate isoforms (including splicing variants) can be detected and cloned from human sources.

OTHER EMBODIMENTS

Included in the invention are: allelic variations; natural mutants; induced mutants; proteins encoded by DNA that hybridizes under high or low stringency conditions to a nucleic acid which encodes a polypeptide of SEQ ID NO:2 (for definitions of high and low stringency see Current Protocols in Molecular Biology, John Wiley & Sons, New York, 1989, 6.3.1–6.3.6, hereby incorporated by reference); and, polypeptides specifically bound by antisera to S4BP.

Nucleic acids and polypeptides of the invention include those that differ from the sequences disclosed herein by virtue of sequencing errors in the disclosed sequences.

The invention also includes fragments, preferably biologically active fragments, or analogs of S4BP. A biologically active fragment or analog is one having any in vivo or in vitro activity which is characteristic of S4BP shown in SEQ ID NO:2, or of other naturally occurring S4BP, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Particularly preferred fragments are fragments e.g., active fragments, which are generated by proteolytic cleavage or alternative splicing events.

Other embodiments are within the following claims.

What is claimed is:

1. An isolated polypeptide comprising an amino acid sequence having at least 80% sequence identity to the amino acid sequence of SEQ ID NO:2, wherein the polypeptide has one or more of the following activities:
    (a) binds syndecan-4;
    (b) binds protein kinase C α (PKCα);
    (c) binds paxillin;
    (d) binds His-5; and
    (e) enhances actin stress fiber and focal contact formation in the absence of serum when expressed in a cell.

2. The polypeptide of claim 1 wherein the polypeptide has at least 85% sequence identity to the amino acid sequence of SEQ ID NO:2.

3. The polypeptide of claim 1 wherein the polypeptide has at least 90% sequence identity to the amino acid sequence of SEQ ID NO:2.

4. The polypeptide of claim 1 wherein the polypeptide has at least 95% sequence identity to the amino acid sequence of SEQ ID NO:2.

5. The polypeptide of claim 1 wherein the polypeptide has at least 96% sequence identity to the amino acid sequence of SEQ ID NO:2.

6. The polypeptide of claim 1 wherein the polypeptide has at least 97% sequence identity to the amino acid sequence of SEQ ID NO:2.

7. The polypeptide of claim 1 wherein the polypeptide has at least 98% sequence identity to the amino acid sequence of SEQ ID NO:2.

8. The polypeptide of claim 1 wherein the polypeptide has at least 99% sequence identity to the amino acid sequence of SEQ ID NO:2.

9. A fusion protein comprising the polypeptide of claim 1 and a heterologous amino acid sequence.

10. An isolated polypeptide comprising the amino acid sequence of SEQ ID NO:2.

11. An isolated polypeptide which is encoded by a nucleic acid molecule comprising a nucleotide sequence having at least 80% sequence identity to the nucleotide sequence of SEQ ID NO:1, or SEQ ID NO:3, wherein the polypeptide has one or more of the following activities:
    (a) binds syndecan-4;
    (b) binds protein kinase C α (PKCα);
    (c) binds paxillin;
    (d) binds His-5; and
    (e) enhances actin stress fiber and focal contact formation in the absence of serum when expressed in a cell.

12. The polypeptide of claim 11 wherein the polypeptide is encoded by a nucleic acid molecule comprising a nucleotide sequence having at least 85% sequence identity to the nucleotide sequence of SEQ ID NO:1 or SEQ ID NO:3.

13. The polypeptide of claim 11 wherein the polypeptide is encoded by a nucleic acid molecule comprising a nucleotide sequence having at least 90% sequence identity to the nucleotide sequence of SEQ ID NO:1 or SEQ ID NO:3.

14. The polypeptide of claim 11 wherein the polypeptide is encoded by a nucleic acid molecule comprising a nucleotide sequence having at least 95% sequence identity to the nucleotide sequence of SEQ ID NO:1 or SEQ ID NO:3.

15. The polypeptide of claim 11 wherein the polypeptide is encoded by a nucleic acid molecule comprising a nucleotide sequence having at least 96% sequence identity to the nucleotide sequence of SEQ ID NO:1 or SEQ ID NO:3.

16. The polypeptide of claim 11 wherein the polypeptide is encoded by a nucleic acid molecule comprising a nucleotide sequence having at least 97% sequence identity to the nucleotide sequence of SEQ ID NO:1 or SEQ ID NO:3.

17. The polypeptide of claim 11 wherein the polypeptide is encoded by a nucleic acid molecule comprising a nucleotide sequence having at least 98% sequence identity to the nucleotide sequence of SEQ ID NO:1 or SEQ ID NO:3.

18. The polypeptide of claim 11 wherein the polypeptide is encoded by a nucleic acid molecule comprising a nucleotide sequence having at least 99% sequence identity to the nucleotide sequence of SEQ ID NO:1 or SEQ ID NO:3.

19. A fusion protein comprising the polypeptide of claim 11 and a heterologous amino acid sequence.

20. An isolated polypeptide encoded by a nucleic acid molecule that hybridizes to a nucleic acid molecule consisting of SEQ ID NO:1 or SEQ ID NO:3 in 6×sodium chloride/sodium citrate (SSC) at about 45° C., followed by one or more washes in 0.2×SSC, 0.1% SDS at 50–65° C., wherein the polypeptide has one or more of the following activities:

(a) binds syndecan-4;

(b) binds protein kinase C α (PKCα);

(c) binds paxillin;

(d) binds His-5; and (e) enhances actin stress fiber and focal contact formation in the absence of serum when expressed in a cell.

21. A fusion protein comprising the polypeptide of claim 20 and a heterologous amino acid sequence.

22. An isolated polypeptide comprising a fragment of SEQ ID NO:2, wherein the fragment comprises at least 15 contiguous amino acids of SEQ ID NO:2 and wherein the fragment has one or more of the following activities:

(a) binds syndecan-4;

(b) binds protein kinase C α (PKCα);

(c) binds paxillin;

(d) binds His-5; and (e) enhances actin stress fiber and focal contact formation in the absence of serum when expressed in a cell.

23. A fusion protein comprising the polypeptide of claim 22 and a heterologous amino acid sequence.

24. An isolated polypeptide that differs from the amino acid sequence of SEQ ID NO:2 by 1 to 40 amino acid residues, wherein the polypeptide has one or more of the following activities:

(a) binds syndecan-4;

(b) binds protein kinase C α (PKCα);

(c) binds paxillin;

(d) binds His-5; and (e) enhances actin stress fiber and focal contact formation in the absence of serum when expressed in a cell.

25. A fusion protein comprising the polypeptide of claim 24 and a heterologous amino acid sequence.

* * * * *

SEQUENCE LISTING

```
<160> NUMBER OF SEQ ID NOS: 7

<210> SEQ ID NO 1
<211> LENGTH: 1182
<212> TYPE: DNA
<213> ORGANISM: Gallus gallus
<220> FEATURE:
<221> NAME/KEY: CDS
<222> LOCATION: (33)...(992)

<400> SEQUENCE: 1
ggcacgagcg cccgcccgcc ggcggcgagg cg atg gcg gcc atg gga gcc atg        53
                                    Met Ala Ala Met Gly Ala Met
                                     1               5 gga gtg atg gcg gcc gta gga gcg ttg ccg gcg ggc gcg ggg tcc ctc        101
Gly Val Met Ala Ala Val Gly Ala Leu Pro Ala Gly Ala Gly Ser Leu
         10                  15                  20 ccg ccg ctg ccg acg ctg ggg gtg ccc ggc gtg ccc gag ctg aag ccg        149
Pro Pro Leu Pro Thr Leu Gly Val Pro Gly Val Pro Glu Leu Lys Pro
     25                  30                  35 ctg acg cgg tac gag gcc atg cgg ctg ggc ccg ggc tgg agc cac tcg        197
Leu Thr Arg Tyr Glu Ala Met Arg Leu Gly Pro Gly Trp Ser His Ser
 40                  45                  50                  55 tgc cac gcc atg ctg tac gcg ccc aac ccg ggc atg ctg ttc ggc cgc        245
Cys His Ala Met Leu Tyr Ala Pro Asn Pro Gly Met Leu Phe Gly Arg
                 60                  65                  70 atc ccg ctg cgc tac gcc gtg ctg atg cag atg cgc ttt gac ggc cta        293
Ile Pro Leu Arg Tyr Ala Val Leu Met Gln Met Arg Phe Asp Gly Leu
             75                  80                  85 ctg ggc ttc ccc ggg ggg ttc gtg gac cgc cgg tac tgg tcc ctg gag        341
Leu Gly Phe Pro Gly Gly Phe Val Asp Arg Arg Tyr Trp Ser Leu Glu
         90                  95                 100 gac ggt ctg aac cgg gtg ctg ggc ctg ggc ctg ggc tgc gtg cgc ctg        389
Asp Gly Leu Asn Arg Val Leu Gly Leu Gly Leu Gly Cys Val Arg Leu
     105                 110                 115
```

-continued

```
acg gag gcc gac tac ctg tgc tcg cac ctg acg gac ggg ccg cat cgc      437
Thr Glu Ala Asp Tyr Leu Cys Ser His Leu Thr Asp Gly Pro His Arg
120                 125                 130                 135 gtg gtg gct cac tta tac gcc cgg cag ctg acc ctg gag gag ctg cac      485
Val Val Ala His Leu Tyr Ala Arg Gln Leu Thr Leu Glu Glu Leu His
                140                 145                 150 acc atc gag atc agc gcg gtg cac tcc cga gac cac ggg ctg gag gtg      533
Thr Ile Glu Ile Ser Ala Val His Ser Arg Asp His Gly Leu Glu Val
            155                 160                 165 atg ggc atg gtc cgt gtc ccc ctc tac acc cag aaa gat cgc atg ggt      581
Met Gly Met Val Arg Val Pro Leu Tyr Thr Gln Lys Asp Arg Met Gly
        170                 175                 180 ggg ctg cca aac ttc ctg gcc aac tcc ttc gtt gga act gcc aaa ttc      629
Gly Leu Pro Asn Phe Leu Ala Asn Ser Phe Val Gly Thr Ala Lys Phe
    185                 190                 195 cag ctg ctc ttt gct ctg aag atc ttg aac atg gtg ccg gag gag aag      677
Gln Leu Leu Phe Ala Leu Lys Ile Leu Asn Met Val Pro Glu Glu Lys
200                 205                 210                 215 ctg gcc gag gcg gtg gct gcc acg cag aag ccg aag aag ccg gcg atc      725
Leu Ala Glu Ala Val Ala Ala Thr Gln Lys Pro Lys Lys Pro Ala Ile
                220                 225                 230 gac cac gcg gct gtg gca gca gca aag cag gcg aac gag ctg gcg gcg      773
Asp His Ala Ala Val Ala Ala Ala Lys Gln Ala Asn Glu Leu Ala Ala
            235                 240                 245 gcc gcc aga gca ggc aat gaa tac gca gat agc gga gag aac cag gca      821
Ala Ala Arg Ala Gly Asn Glu Tyr Ala Asp Ser Gly Glu Asn Gln Ala
        250                 255                 260 gct gcg cac gct gcg gcc gag ctg gca gag cag cag gcg gcc ggg ctg      869
Ala Ala His Ala Ala Ala Glu Leu Ala Glu Gln Gln Ala Ala Gly Leu
    265                 270                 275 gag agc cag gct gtg ctg gag cat ctg gcg gcc gtg ccg ggg gct gag      917
Glu Ser Gln Ala Val Leu Glu His Leu Ala Ala Val Pro Gly Ala Glu
280                 285                 290                 295 gcc gtg gtg gcg gag ctg cac gcg cag ccc ggg gca gac gct gtg ctg      965
Ala Val Val Ala Glu Leu His Ala Gln Pro Gly Ala Asp Ala Val Leu
                300                 305                 310 gag cag ccg gtg gct gag gcc atg gag tgatgccccc gtgtttgtaa           1012
Glu Gln Pro Val Ala Glu Ala Met Glu
            315                 320 ttgattaaaa gtgggtgagg agactagaga ctttcttcta acttcccaac cagttgctgg   1072
ctgcgagatt ccgctgtgta gccaggaggg tttggaattg tctgaagcag gggaaagcta   1132
tgtattttta tggccattaa actctagcga gcttcccaga tcaaaaaaaa              1182

<210> SEQ ID NO 2
<211> LENGTH: 320
<212> TYPE: PRT
<213> ORGANISM: Gallus gallus

<400> SEQUENCE: 2

Met Ala Ala Met Gly Ala Met Gly Val Met Ala Val Gly Ala Leu
1               5                   10                  15

Pro Ala Gly Ala Gly Ser Leu Pro Pro Leu Pro Thr Leu Gly Val Pro
                20                  25                  30

Gly Val Pro Glu Leu Lys Pro Leu Thr Arg Tyr Glu Ala Met Arg Leu
            35                  40                  45

Gly Pro Gly Trp Ser His Ser Cys His Ala Met Leu Tyr Ala Pro Asn
        50                  55                  60
```

```
Pro Gly Met Leu Phe Gly Arg Ile Pro Leu Arg Tyr Ala Val Leu Met
65                  70                  75                  80

Gln Met Arg Phe Asp Gly Leu Leu Gly Phe Pro Gly Gly Phe Val Asp
                85                  90                  95

Arg Arg Tyr Trp Ser Leu Glu Asp Gly Leu Asn Arg Val Leu Gly Leu
            100                 105                 110

Gly Leu Gly Cys Val Arg Leu Thr Glu Ala Asp Tyr Leu Cys Ser His
        115                 120                 125

Leu Thr Asp Gly Pro His Arg Val Val Ala His Leu Tyr Ala Arg Gln
130                 135                 140

Leu Thr Leu Glu Glu Leu His Thr Ile Glu Ile Ser Ala Val His Ser
145                 150                 155                 160

Arg Asp His Gly Leu Glu Val Met Gly Met Val Arg Val Pro Leu Tyr
                165                 170                 175

Thr Gln Lys Asp Arg Met Gly Gly Leu Pro Asn Phe Leu Ala Asn Ser
            180                 185                 190

Phe Val Gly Thr Ala Lys Phe Gln Leu Leu Phe Ala Leu Lys Ile Leu
        195                 200                 205

Asn Met Val Pro Glu Glu Lys Leu Ala Glu Ala Val Ala Ala Thr Gln
210                 215                 220

Lys Pro Lys Pro Ala Ile Asp His Ala Ala Val Ala Ala Ala Ala Lys
225                 230                 235                 240

Gln Ala Asn Glu Leu Ala Ala Ala Ala Arg Ala Gly Asn Glu Tyr Ala
                245                 250                 255

Asp Ser Gly Glu Asn Gln Ala Ala Ala His Ala Ala Ala Glu Leu Ala
            260                 265                 270

Glu Gln Gln Ala Ala Gly Leu Glu Ser Gln Ala Val Leu Glu His Leu
        275                 280                 285

Ala Ala Val Pro Gly Ala Glu Ala Val Val Ala Glu Leu His Ala Gln
290                 295                 300

Pro Gly Ala Asp Ala Val Leu Glu Gln Pro Val Ala Glu Ala Met Glu
305                 310                 315                 320

<210> SEQ ID NO 3
<211> LENGTH: 960
<212> TYPE: DNA
<213> ORGANISM: Gallus gallus

<400> SEQUENCE: 3
atggcggcca tgggagccat gggagtgatg gcggccgtag gagcgttgcc ggcgggcgcg      60
gggtccctcc cgccgctgcc gacgctgggg gtgcccggcg tgcccgagct gaagccgctg     120
acgcggtacg aggccatgcg gctgggcccg ggctggagcc actcgtgcca cgccatgctg     180
tacgcgccca cccgggcat gctgttcggc cgcatcccgc tgcgctacgc cgtgctgatg      240
cagatgcgct tgacggcct actgggcttc ccgggggggt cgtggaccg ccggtactgg       300 tccctggagg acgtctgaa ccgggtgctg ggcctgggc tgggctgcgt gcgcctgacg       360
gaggccgact acctgtgctc gcacctgacg gacgggccgc atcgcgtggt ggctcactta    420
tacgcccggc agctgaccct ggaggagctg cacaccatcg agatcagcgc ggtgcactcc    480
cgagaccacg gcctggaggt gatgggcatg gtccgtgtcc ccctctacac ccagaaagat    540
cgcatgggtg gctgccaaa cttcctggcc aactccttcg ttggaactgc caaattccag    600
ctgctctttg ctctgaagat cttgaacatg gtgccggagg agaagctggc cgaggcggtg    660
```

-continued

```
gctgccacgc agaagccgaa gaagccggcg atcgaccacg cggctgtggc agcagcaaag      720
caggcgaacg agctggcggc ggccgccaga gcaggcaatg aatacgcaga tagcggagag      780
aaccaggcag ctgcgcacgc tgcggccgag ctggcagagc agcaggcggc cgggctggag      840
agccaggctg tgctggagca tctggcggcc gtgccggggg ctgaggccgt ggtggcggag      900
ctgcacgcgc agcccggggc agacgctgtg ctggagcagc cggtggctga ggccatggag      960
```

<210> SEQ ID NO 4
<211> LENGTH: 876
<212> TYPE: DNA
<213> ORGANISM: Gallus gallus

<400> SEQUENCE: 4

```
caggagtcgg attctgttcc gttccgattc agcgctccgc accgcctcgc ttcgccatgc       60
cgctgccccg cgccgcgttc ctgctcggcc tcctgctggc cgctgccgcc gccgagtcgg      120
tgagagaaac agagaccatg gatgcccgat ggcttgacaa cgtgggctct ggagacctgc      180
cagatgatga agacattggt gaattcacac ctcacttaac ttctgacgag tttgatatag      240
atgacacatc tggctccgga gactactcag attatgatga tgccatatac ctgaccactg      300
tggatactcc tgcaatatct gacaactata ccctggaga tacagagaga agatggaag      360 gtgagaagaa aaacaccatg ctggacaatg aaatcattcc agacaaagct tcacctgttg      420
aagcaaacct gtccaacaag atctccatgg caagcacagc caacagcagc atctttgaaa      480
gaacagaagt tcttacagct ctcattgcag gaggagcagt tggcctcctg tttgctgtct      540
tcctgatcct cctcttagtc tatcgcatga gaaaaagga cgaggcagc tacgaccttg      600 ggaagaaacc catctacaag aaagccccta caaatgagtt ctacgcttaa agctctgtgc      660
cccttgggac aaatggaccg tatggaaaca ctgtgccctc caatgagacg tgctgaacaa      720
acgctctttt tggattgaat ttcaaagtga cttttgaggg tggggacca aactttctac      780 gtgaccccacc ccgctcagct aacaagggtc aatggaata caaagagtct ggggggggg      840 ttgggggga gcctcggcgg tgtatctttt tttttt                                 876
```

<210> SEQ ID NO 5
<211> LENGTH: 197
<212> TYPE: PRT
<213> ORGANISM: Gallus gallus

<400> SEQUENCE: 5

```
Met Pro Leu Pro Arg Ala Ala Phe Leu Leu Gly Leu Leu Leu Ala Ala
 1               5                   10                  15

Ala Ala Ala Glu Ser Val Arg Glu Thr Glu Thr Met Asp Ala Arg Trp
                20                  25                  30

Leu Asp Asn Val Gly Ser Gly Asp Leu Pro Asp Asp Glu Asp Ile Gly
            35                  40                  45

Glu Phe Thr Pro His Leu Thr Ser Asp Glu Phe Asp Ile Asp Asp Thr
        50                  55                  60

Ser Gly Ser Gly Asp Tyr Ser Asp Tyr Asp Asp Ala Ile Tyr Leu Thr
 65                  70                  75                  80

Thr Val Asp Thr Pro Ala Ile Ser Asp Asn Tyr Ile Pro Gly Asp Thr
                85                  90                  95

Glu Arg Lys Met Glu Gly Glu Lys Lys Asn Thr Met Leu Asp Asn Glu
            100                 105                 110

Ile Ile Pro Asp Lys Ala Ser Pro Val Glu Ala Asn Leu Ser Asn Lys
        115                 120                 125
```

```
Ile Ser Met Ala Ser Thr Ala Asn Ser Ser Ile Phe Glu Arg Thr Glu
        130                 135                 140

Val Leu Thr Ala Leu Ile Ala Gly Gly Ala Val Gly Leu Leu Phe Ala
145                 150                 155                 160

Val Phe Leu Ile Leu Leu Val Tyr Arg Met Lys Lys Lys Asp Glu
                165                 170                 175

Gly Ser Tyr Asp Leu Gly Lys Lys Pro Ile Tyr Lys Lys Ala Pro Thr
                180                 185                 190

Asn Glu Phe Tyr Ala
            195

<210> SEQ ID NO 6
<211> LENGTH: 29
<212> TYPE: PRT
<213> ORGANISM: Gallus gallus

<400> SEQUENCE: 6

Gly Met Val Arg Val Pro Leu Tyr Thr Gln Lys Asp Arg Met Gly Gly
1               5                   10                  15

Leu Pro Asn Phe Leu Ala Asn Ser Phe Val Gly Thr Ala
                20                  25

<210> SEQ ID NO 7
<211> LENGTH: 13
<212> TYPE: RNA
<213> ORGANISM: Artificial Sequence
<220> FEATURE:
<223> OTHER INFORMATION: Consensus sequence

<400> SEQUENCE: 7
gccgccrcca ugg                                                          13
```